US011666636B2

(12) United States Patent
Niswender et al.

(10) Patent No.: US 11,666,636 B2
(45) Date of Patent: Jun. 6, 2023

(54) GLP-1R AGONISTS AND USES THEREOF

(71) Applicant: VANDERBILT UNIVERSITY, Nashville, TN (US)

(72) Inventors: Kevin Niswender, Nashville, TN (US); Stokes Peebles, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 124 days.

(21) Appl. No.: 16/485,190

(22) PCT Filed: Feb. 14, 2018

(86) PCT No.: PCT/US2018/018136
§ 371 (c)(1),
(2) Date: Aug. 12, 2019

(87) PCT Pub. No.: WO2018/152172
PCT Pub. Date: Aug. 23, 2018

(65) Prior Publication Data
US 2019/0358299 A1    Nov. 28, 2019

Related U.S. Application Data

(60) Provisional application No. 62/458,744, filed on Feb. 14, 2017.

(51) Int. Cl.
*A61K 38/26* (2006.01)
*A61P 31/14* (2006.01)

(52) U.S. Cl.
CPC .............. *A61K 38/26* (2013.01); *A61P 31/14* (2018.01)

(58) Field of Classification Search
CPC ................................ A61K 38/26; A61P 31/14
See application file for complete search history.

(56) References Cited

U.S. PATENT DOCUMENTS

| 8,614,182 B2 | 12/2013 | Wang et al. | |
| 8,758,761 B2 | 6/2014 | Atkinson et al. | |
| 2017/0326208 A1* | 11/2017 | Fallon ............ | C12Y 301/27001 |

FOREIGN PATENT DOCUMENTS

| WO | 2006097538 | 9/2006 |
| WO | 2007113205 | 10/2007 |

OTHER PUBLICATIONS

Viby et al., Endocrinology, Dec. 2013, 154(12):4503-4511 (Year: 2013).*
Borish, Ann Allergy Asthma Immunol, 117 (2016) 108-114 (Year: 2016).*
Papadopoulos et al. Clinical and Translational Allergy 2012, 2:21 (Year: 2012).*
Zhu et al., Int. Jl. Mol. Sci., 2015, 16, 20195-20211 (Year: 2015).*
Toki et al., J. Allergy Clin Immunol., vol. 139, No. 2, p. AB81, Abstract 258, Feb. 1, 2017 (Year: 2017).*
Salo et al., J Allergy Clin Immunol. Oct. 2006 ; 118(4): 892-898 (Year: 2006).*
Bates et al., Am J Physiol Lung Cell Mol Physiol. Sep. 2009; 297(3): L401-L410 (Year: 2009).*
Bang-Berthelsen et al., Inflamm Bowel Dis 2016;22:2078-2097 (Year: 2016).*
Kamijo et al., J Immunol 2013; 190:4489-4499 (Year: 2013).*
Marino et al., American Journal of Health-System Pharmacy, vol. 71, Issue 3, Feb. 1, 2014, pp. 223-226 (Year: 2014).*
Grob et al., Inflamm Bowel Dis 2012;18:1900-1909 (Year: 2012).*
Li X, Ampleford EJ, Howard TD, Moore WC, Torgerson DG, Li H, et al. Genome-wide association studies of asthma indicate opposite immunopathogenesis direction from autoimmune diseases. J Allergy Clin Immunol 2012; 130: 861-868.
Nieuwenhuis MA, Siedlinski M, van den Berge M, Granell R, Li X, Niens M, et al. Combining genomewide association study and lung eQTL analysis provides evidence for novel genes associated with asthma. Allergy; Aug. 22, 2016.
Ober C, Yao T-C. The genetics of asthma and allergic disease: a 21st century perspective. Immunological Reviews 2011; 242:10-30.
Savenije OE, Mahachie John JM, Granell R, Kerkhof M, Dijk FN, de Jongste JC, et al. Association of IL33-IL-1 receptor-like 1 (IL1RL1) pathway polymorphisms with wheezing phenotypes and asthma in childhood. J Allergy Clin Immunol 2014; 134: 170-177.
Hristova M, Habibovic A, Veith C, Janssen-Heininger YM, Dixon AE, Geiszt M, et al. Airway epithelial dual oxidase 1 mediates allergen-induced IL-33 secretion and activation of type 2 immune responses. J Allergy Clin Immunol 2015; 137:1545-1556.
Halim Timotheus YF, Krauß Ramona H, Sun Ann C, Takei F. Lung Natural Helper Cells Are a Critical Source of Th2 Cell-Type Cytokines in Protease Allergen-Induced Airway Inflammation. Immunity 2012; 36: 451-463.
Bartemes KR, Iijima K, Kobayashi T, Kephart GM, McKenzie AN, Kita H. IL-33-responsive lineage—CD25+ CD44(hi) lymphoid cells mediate innate type 2 immunity and allergic inflammation in the lungs. J Immunol 2012; 188: 1503-1513.
Kurowska-Stolarska M, Kewin P, Murphy G, Russo RC, Stolarski B, Garcia CC, et al. IL-33 induces antigen-specific IL-5+ T cells and promotes allergic-induced airway inflammation independent of IL-4. J Immunol 2008; 181: 4780-90.
Borish L. The immunobiology of asthma: Asthma phenotypes and their implications for personalized treatment. Ann Allergy Asthma Immunol 2016; 117:108-114.
Lim GE, Brubaker PL. Glucagon-Like Peptide 1 Secretion by the L-Cell: The View From Within. Diabetes 2006; 55: S70-S77.
Vilsboll T, Toft-Nielsen MB, Krarup T, Madsbad S, Dinesen B, Holst JJ. Evaluation of beta-cell secretory capacity using glucagon-like peptide 1. Diabetes Care 2000; 23: 807-812.
De Marinis YZ, Salehi A, Ward CE, Zhang Q, Abdulkader F, Bengtsson M, et al. GLP-1 inhibits and adrenaline stimulates glucagon release by differential modulation of N- and L-type Ca2+ channel-dependent exocytosis. Cell Metab 2010; 11: 543-553.

(Continued)

*Primary Examiner* — Fred H Reynolds
*Assistant Examiner* — Joseph Fischer
(74) *Attorney, Agent, or Firm* — Meunier Carlin & Curfman LLC

(57) ABSTRACT

The present disclosure relates to glucagon-like peptide-1 receptor (GLP-1R) agonists and methods of treating or preventing allergic inflammation and/or methods of treating or preventing respiratory syncytial virus (RSV) infection.

5 Claims, 21 Drawing Sheets

Specification includes a Sequence Listing.

(56) References Cited

OTHER PUBLICATIONS

Spreckley E, Murphy KG. The L-Cell in Nutritional Sensing and the Regulation of Appetite. Front Nutr 2015; 2: 23.

Egan AG, Blind E, Dunder K, de Graeff PA, Hummer BT, Bourcier T, et al. Pancreatic safety of incretin-based drugs—FDA and EMA assessment. N Engl J Med 2014; 370: 794-797.

Divino V, DeKoven M, Hallinan S, Varol N, Wirta SB, Lee WC, et al. Glucagon-like Peptide-1 receptor agonist treatment patterns among type 2 diabetes patients in six European countries. Diabetes Ther 2014; 5: 499-520.

Hogan AE, Gaoatswe G, Lynch L, Corrigan MA, Woods C, O'Connell J, et al. Glucagon-like peptide 1 analogue therapy directly modulates innate immune-mediated inflammation in individuals with type 2 diabetes mellitus. Diabetologia 2014; 57: 781-784.

Lee YS, Park MS, Choung JS, Kim SS, Oh HH, Choi CS, et al. Glucagon-like peptide-1 inhibits adipose tissue macrophage infiltration and inflammation in an obese mouse model of diabetes. Diabetologia 2012; 55: 2456-2468.

Yanay O, Bailey AL, Kernan K, Zimmerman JJ, Osborne WR. Effects of exendin-4, a glucagon like peptide-1 receptor agonist, on neutrophil count and inflammatory cytokines in a rat model of endotoxemia. J Inflamm Res 2015; 8: 129-135.

Wang Y, Parlevliet ET, Geerling JJ, van der Tuin SJ, Zhang H, Bieghs V, et al. Exendin-4 decreases liver inflammation and atherosclerosis development simultaneously by reducing macrophage infiltration. Br J Pharmacol 2014; 171: 723-734.

Gou S, Zhu T, Wang W, Xiao M, Wang XC, Chen ZH. Glucagon like peptide-1 attenuates bleomycin-induced pulmonary fibrosis, involving the inactivation of NF-kappaB in mice. Int Immunopharmacol 2014; 22: 498-504.

Zhu T, Wu XL, Zhang W, Xiao M. Glucagon Like Peptide-1 (GLP-1) Modulates OVA-Induced Airway Inflammation and Mucus Secretion Involving a Protein Kinase A (PKA)-Dependent Nuclear Factor-kappaB (NF-kappaB) Signaling Pathway in Mice. Int J Mol Sci 2015; 16: 20195-20211.

Kouzaki H, Iijima K, Kobayashi T, O'Grady SM, Kita H. The danger signal, extracellular ATP, is a sensor for an airborne allergen and triggers IL-33 release and innate Th2-type responses. J Immunol 2011; 186:4375-4387.

O'Hollaren MT, Yunginger JW, Offord KP, Somers MJ, O'Connell EJ, Ballard DJ, et al. Exposure to an aeroallergen as a possible precipitating factor in respiratory arrest in young patients with asthma. N Engl J Med 1991; 324:359-63.

Hardman CS, Panova V, McKenzie ANJ. IL-33 citrine reporter mice reveal the temporal and spatial expression of IL-33 during allergic lung inflammation. European Journal of Immunology 2013; 43: 488-498.

Reddy IA, Pino JA, Weikop P, Osses N, Sorensen G, Bering T, et al. Glucagon-like peptide 1 receptor activation regulates cocaine actions and dopamine homeostasis in the lateral septum by decreasing arachidonic acid levels. Transl Psychiatry 2016; 6: e809.

Snelgrove RJ, Gregory LG, Peiró T, Akthar S, Campbell GA, Walker SA, et al. Alternaria-derived serine protease activity drives IL-33-mediated asthma exacerbations. Journal of Allergy and Clinical Immunology 2014; 134: 583-592.e586.

Toki S, Goleniewska K, Reiss S, Zhou W, Newcomb DC, Bloodworth MH, et al. The histone deacetylase inhibitor trichostatin A suppresses murine innate allergic inflammation by blocking group 2 innate lymphoid cell (ILC2) activation. Thorax 2016; 71: 633-645.

Zhu Z, Homer RJ, Wang Z, Chen Q, Geba GP, Wang J, et al. Pulmonary expression of interleukin-13 causes inflammation, mucus hypersecretion, subepithelial fibrosis, physiologic abnormalities, and eotaxin production. J Clin Invest 1999; 103: 779-788.

Pyke C, Heller RS, Kirk RK, Ørskov C, Reedtz-Runge S, Kaastrup P, et al. GLP-1 Receptor Localization in Monkey and Human Tissue: Novel Distribution Revealed With Extensively Validated Monoclonal Antibody. Endocrinology 2014; 155: 1280-1290.

Arakawa M, Mita T, Azuma K, Ebato C, Goto H, Nomiyama T, et al. Inhibition of Monocyte Adhesion to Endothelial Cells and Attenuation of Atherosclerotic Lesion by a Glucagon-like Peptide-1 Receptor Agonist, Exendin-4. Diabetes 2010; 59: 1030-1037.

Parthsarathy V, Hölscher C. The type 2 diabetes drug liraglutide reduces chronic inflammation induced by irradiation in the mouse brain. European Journal of Pharmacology 2013; 700: 42-50.

Iwai T, Ito S, Tanimitsu K, Udagawa S, Oka J-I. Glucagon-like peptide-1 inhibits LPS-induced IL-1β production in cultured rat astrocytes. Neuroscience Research 2006; 55: 352-360.

Viby N-E, Isidor MS, Buggeskov KB, Poulsen SS, Hansen JB, Kissow H. Glucagon-Like Peptide-1 (GLP-1) Reduces Mortality and Improves Lung Function in a Model of Experimental Obstructive Lung Disease in Female Mice. Endocrinology 2013; 154; 4503-4511.

Holst JJ. The physiology of glucagon-like peptide 1. Physiol Rev 2007; 87: 1409-1439.

Billington CK, Ojo OO, Penn RB, Ito S. cAMP regulation of airway smooth muscle function. Pulmonary Pharmacology & Therapeutics 2013; 26: 112-120.

Zhou W, Blackwell TS, Goleniewska K, O'Neal JF, Fitzgerald GA, Lucitt M, et al. Prostaglandin I2 analogs inhibit Th1 and Th2 effector cytokine production by CD4 T cells. J Leukoc Biol 2007; 81: 809-817.

Zhou W, Hashimoto K, Goleniewska K, O'Neal JF, Ji S, Blackwell TS, et al. Prostaglandin I2 analogs inhibit proinflammatory cytokine production and T cell stimulatory function of dendritic cells. J Immunol 2007; 178: 702-710.

Zhou W, Toki S, Zhang J, Goleniewksa K, Newcomb DC, Cephus JY, et al. Prostaglandin I2 Signaling and Inhibition of Group 2 Innate Lymphoid Cell Responses. Am J Respir Crit Care Med 2016; 193: 31-42.

Hung LY, Lewkowich IP, Dawson LA, Downey J, Yang Y, Smith DE, et al. IL-33 drives biphasic IL-13 production for noncanonical Type 2 immunity against hookworms. Proc Natl Acad Sci USA 2013; 110: 282-287.

Kurowska-Stolarska M, Hueber A, Stolarski B, McInnes IB. Interleukin-33: a novel mediator with a role in distinct disease pathologies. Journal of Internal Medicine 2011; 269: 29-35.

Cayrol C, Girard J-P. IL-33: an alarmin cytokine with crucial roles in innate immunity, inflammation and allergy. Current Opinion in Immunology 2014; 31:31-37.

Shiraki A, Oyama J, Komoda H, Asaka M, Komatsu A, Sakuma M, Kodama K et al. The glucagon-like peptide 1 analog liraglutide reduces TNF-alpha-induced oxidative stress and inflammation in endothelial cells. Atherosclerosis 2012; 221:375-382.

Mohapatra A, Dyken SJV, Schneider C, Nussbaum JC, Liang H-E, Locksley RM. Group 2 innate lymphoid cells utilize the IRF4-IL-9 module to coordinate epithelial cell maintenance of lung homeostasis. Mucosal Immunol 2016;1:275-286.

Kurokawa M, Matsukura S, Kawaguchi M, Ieki K, Suzuki S, Odaka M, et al. Expression and Effects of IL-33 and ST2 in Allergic Bronchial Asthma: IL-33 Induces Eotaxin Production in Lung Fibroblasts. International Archives of Allergy and Immunology 2011; 155: 12-20.

Besnard A-G, Togbe D, Guillou N, Erard F, Quesniaux V, Ryffel B. IL-33-activated dendritic cells are critical for allergic airway inflammation. European Journal of Immunology 2011; 41; 1675-1686.

Hogan AE, Tobin AM, Ahem T, Corrigan MA, Gaoatswe G, Jackson R. et al. Glucagon-like peptide-1 (GLP-1) and the regulation of human invariant natural killer T cells: lessons from obesity, diabetes and psoriasis. Diabetologia 2011; 54:2745-2754.

Campbell JE, Drucker DJ. Pharmacology, physiology, and mechanisms of incretin hormone action. Cell Metab. 2013;17(6):819-837. doi:10.1016/j.cmet.2013.04.008.

Marso SP, Daniels GH, Brown-Frandsen K, Kristensen P, Mann JFE, Nauck MA, Nissen SE, Pocock S, Poulter NR, Ravn LS, Steinberg WM, Stockner M, Zinman B, Bergenstal RM, Buse JB, LEADER Steering Committee, LEADER Trial Investigators. Liraglutide and Cardiovascular Outcomes in Type 2 Diabetes. N Engl J Med. 2016;375(4):311-322. doi:10.1056/NEJMoa1603827.

Ahern T, Tobin A-M, Corrigan M, Hogan A, Sweeney C, Kirby B, O'Shea D. Glucagon-like peptide-1 analogue therapy for psoriasis

(56) References Cited

OTHER PUBLICATIONS patients with obesity and type 2 diabetes: a prospective cohort study. J Eur Acad Dermatol Venereol. 2013;27(11):1440-1443. doi:10.1111/j.1468-3083.2012.04609.x.

Zhu T, Wu X-L, Zhang W, Xiao M. Glucagon Like Peptide-1 (GLP-1) Modulates OVA-Induced Airway Inflammation and Mucus Secretion Involving a Protein Kinase A (PKA)-Dependent Nuclear Factor-κB (NF-κB) Signaling Pathway in Mice. Int J Mol Sci. 2015;16(9):20195-20211. doi:10.3390/ijms160920195.

Johnson JE, Gonzales RA, Olson SJ, Wright PF, Graham BS. The histopathology of fatal untreated human respiratory syncytial virus infection. Mod Pathol. 2007;20(1):108-119. doi:10.1038/modpathol.3800725.

DeVincenzo JP, El Saleeby CM, Bush AJ. Respiratory syncytial vims load predicts disease severity in previously healthy infants. J Infect Dis. 2005;191(11):1861-1868. doi:10.1086/430008.

Simonis-Bik AM, Nijpels G, van Haeften TW, Houwing-Duistermaat JJ, Boomsma DI, Reiling E, van Hove EC, Diamant M, Kramer MHH, Heine RJ, Maassen JA, Slagboom PE, Willemsen G, Dekker JM, Eekhoff EM, de Geus EJ, 't Hart LM. Gene Variants in the Novel Type 2 Diabetes Loci CDC123/CAMK1D, THADA, ADAMTS9, BCL11A, and MTNR1B Affect Different Aspects of Pancreatic-Cell Function. Diabetes. 2010;59(1):293-301. doi:10.2337/db09-1048.

Denny JC, Bastarache L, Ritchie MD, Carroll RJ, Zink R, Mosley JD, Field JR, Pulley JM, Ramirez AH, Bowton E, Basford MA, Carrell DS, Peissig PL, Kho AN, Pacheco JA, Rasmussen L V, Crosslin DR, Crane PK, Pathak J, Bielinski SJ, Pendergrass SA, Xu H, Hindorff LA, Li R, Manolio TA, Chute CG, Chisholm RL, Larson EB, Jarvik GP, Brilliant MH, McCarty CA, Kullo IJ, Haines JL, Crawford DC, Masys DR, Roden DM. Systematic comparison of phenome-wide association study of electronic medical record data and genome-wide association study data. Nat Biotechnol. 2013;31(12):1102-1111. doi:10.1038/nbt.2749.

Borish L. The immunology of asthma: Asthma phenotypes and their implications for personalized treatment. Ann Allergy Asthma Immunol. 2016;117(2):108-114. doi:10.1016/j.anai.2016.04.022.

Larkin, E. K. et al. Objectives, design and enrollment results from the Infant Susceptibility to Pulmonary Infections and Asthma Following RSV Exposure Study (INSPIRE). BMC Pulm. Med. 15, 45 (2015).

Dulek, D. E. et al. STAT4 Deficiency Fails To Induce Lung Th2 or Th17 Immunity following Primary or Secondary Respiratory Syncytial Virus (RSV) Challenge but Enhances the Lung RSV-Specific CD8+ T Cell Immune Response to Secondary Challenge. J. Virol. 88, 9655-72 (2014).

Hardman, C. S., Panova, V. & McKenzie, A. N. J. IL-33 citrine reporter mice reveal the temporal and spatial expression of IL-33 during allergic lung inflammation. Eur. J. Immunol. 43, 488-98 (2013).

Animals, N. R. C. (US) C. for the U. of the G. for the C. and U. of L. Guide for the Care and Use of Laboratory Animals. (National Academies Press, 2011). doi:10.17226/12910.

Graham, B. S., Perkins, M. D., Wright, P. F. & Karzon, D. T. Primary respiratory syncytial virus infection in mice. J. Med. Virol. 26, 153-62 (1988).

Peebles, R. S., Sheller, J. R., Johnson, J. E., Mitchell, D. B. & Graham, B. S. Respiratory syncytial virus infection prolongs methacholine-induced airway hyperresponsiveness in ovalbumin-sensitized mice. J. Med. Virol. 57, 186-92 (1999).

Peebles, R. S et al. Respiratory syncytial virus infection does not increase allergen147 induced type 2 cytokine production, yet increases airway hyperresponsiveness in mice. J. Med. Virol. 63, 178-88 (2001).

Kodani, M. et al. Application of TaqMan low-density arrays for simultaneous detection of multiple respiratory pathogens. J. Clin. Microbiol. 49, 2175-82 (2011).

Bates, J. T. et al. Reversion of somatic mutations of the respiratory syncytial virus specific human monoclonal antibody Fab19 reveal a direct relationship between association rate and neutralizing potency. J. Immunol. 190, 3732-9 (2013).

Roden, D. et al. Development of a Large-Scale De-Identified DNA Biobank to Enable Personalized Medicine. Clin. Pharmacol. Ther. 84, 362-369 (2008).

Denny, J. C. et al. Systematic comparison of phenome-wide association study of electronic medical record data and genome-wide association study data. Nat. Biotechnol. 31, 1102-1111 (2013).

Carroll, R. J., Bastarache, L. & Denny, J. C. R PheWAS: data analysis and plotting tools for phenome-wide association studies in the R environment. Bioinformatics 30, 2375-2376 (2014).

Drucker D J, Nauck M A. The incretin system: glucagon-like peptide-1 receptor agonists and dipeptidyl peptidase-4 inhibitors in type 2 diabetes. Lancet. 2006, 368(9548):1696-1705.

International Search Report and Written Opinion dated Apr. 26, 2018, from International Application No. PCT/US2018/018136, 52 pages.

Viby, N. et al. "Glucagon-Like Peptide-1 (GLP-1) Reduces Mortality and Improves Lung Function in a Model of Experimental Obstructive Lung Disease in Female Mice", Endocrinology, Dec. 2013, 154(12):4503-4511.

Toki, S. et al. "Glucagon-like Peptide 1 Receptor (GLP-1R) Signaling Inhibits Aeroallergen-Induced IL-33 Release and Reduces Group 2 Innate Lymphoid Cell (ILC2) Activation In Vivo", The Journal of Allergy and Clinical Immunology, Feb. 1, 2017, vol. 139, No. 2, AB81.

Peebles, S. et al. "Glucagon-like Peptide-1 receptor signaling attenuates RSV-induced type 2 responses and immunopathology", The Journal of Allergy and Clinical Immunology, Feb. 1, 2017, vol. 139, No. 2, AB270.

Kim, HK et al. "Innate Type 2 Response to Alternaria Extract Enhances Ryegrass-induced Lung Inflammation", International Archives of Allergy and Immunology, 2014, vol. 163, No. 2, pp. 92-105.

Nials, AT et al. "Mouse models of allergic asthma: acute and chronic allergen challenge", Disease Models and Mechanisms, Nov.-Dec. 2008, vol. 1, No. 4-5, pp. 213-220.

Doras, Camille et al., Lung responses in murine models of experimental asthma: Value of house dust mite over ovalbumin sensitization, Respiratory Physiology & Neurobiology, Sep. 8, 2017, pp. 43-51, vol. 247.

* cited by examiner

GLP-1R AGONISTS AND USES THEREOF

CROSS REFERENCE TO RELATED APPLICATIONS

This application is a national stage application filed under 35 U.S.C. § 371 of PCT/US2018/018136 filed Feb. 14, 2018, which claims the benefit of U.S. Provisional Patent Application Serial No. 62/458,744 filed Feb. 14, 2017, which are is expressly incorporated herein by reference in their its entirety.

STATEMENT REGARDING FEDERALLY SPONSORED RESEARCH

This invention was made with government support under Grant No. UL1 RR024975-01 awarded by the National Center for Research Resources and Grant No. 2 UL1 TR000445-06 awarded by the National Center for Advancing Translational Sciences. The Government has certain rights in the invention.

FIELD

The present disclosure relates to glucagon-like peptide-1 receptor (GLP-1R) agonists and methods of treating or preventing allergic inflammation and/or methods of treating or preventing respiratory syncytial virus (RSV) infection.

BACKGROUND

IL-33 is one of the most consistently associated gene candidates for asthma identified by genome wide association studies (GWAS) in diverse ethnic groups. IL-33 is predominantly produced by epithelial cells in response to protease containing aeroallergens and its release is mediated by dual oxidase 1 (DUOX1). IL-33 activates group 2 innate lymphoid cells (ILC2) to produce the type 2 cytokines IL-5 and IL-13 that initiate innate immunity-driven allergic responses. In addition, IL-33 polarizes naïve CD4 T cells to differentiate into effector T helper 2 (Th2) cells, which produce IL-4, IL-5, and IL-13 that are responsible for adaptive immunity-mediated allergen-induced responses. Therefore, IL-33 is a central mediator of both innate and adaptive immunity regulated allergic inflammation in the lung that have a role in the pathogenesis of conditions such as asthma, and IL-33 has been deemed to be an important therapeutic target in inhibiting allergic diseases. However, there have been no reports identifying pharmacologic agents which inhibit lung IL-33 protein release or expression.

Glucagon-like peptide-1 (GLP-1) is a peptide hormone synthesized and released by enteroendocrine L-cells in the ileum and large intestine following oral food intake. GLP-1 has a role in glycemic control by inducing glucose-dependent insulin secretion from β-cells and inhibiting glucagon release from α-cells in the pancreas. GLP-1 also induces weight loss by promoting satiety. GLP-1 receptor (GLP-1R) agonists, such as liraglutide and exenatide are approved by the Food and Drug Administration (FDA) for treatment of type 2 diabetes (T2D).

Several studies report that GLP-1R agonists had anti-inflammatory effects in multiple disorders including T2D. For instance, GLP-1R agonist administration decreased TNFα and IL-6 production by peripheral blood mononuclear cells (PBMC) of obese patients with T2D and diabetic mouse adipose tissue. In addition, the GLP-1R agonist, exendin-4, reduced serum inflammatory cytokines during LPS-induced endotoxemia, liver inflammation, and aortic atherosclerosis in a rodent model. These data indicate that GLP-1R agonists down-regulate innate inflammatory responses to endotoxins or endogenous inflammatory mediators. Further, it has been reported that liraglutide attenuated bleomycin-induced pulmonary fibrosis and OVA-induced chronic airway inflammation. However, no studies have reported the effect of GLP-1R agonists on lung IL-33 expression or release, the effect of GLP-1R agonists on the innate allergic inflammatory response that is mediated by ILC2, or the effect of GLP-1R agonists on respiratory syncytial virus (RSV) infection.

The compounds, compositions, and methods disclosed herein address these and other needs.

SUMMARY

Disclosed herein are methods of treating allergic disorders and respiratory syncytial virus (RSV) infections with a glucagon-like peptide-1 receptor (GLP-1R) agonist. The inventors found that GLP-1R agonists inhibited IL-33 expression and release from the lungs of mice in response to an airway challenge the allergen extract of the aeroallergen *Alternaria alternata*, an aeroallergen which has protease activity and which is associated with severe asthma exacerbations. This is the first study to identify an FDA approved pharmacologic agent that inhibits lung IL-33 release, providing an alternative to biologic therapies that target IL-33-mediated diseases.

In some aspects, disclosed herein is a method of treating or preventing an allergic disease in a subject who has, or is at risk of developing an allergic disease, comprising administering to the subject a therapeutically effective amount of a glucagon-like peptide-1 receptor (GLP-1Rt) agonist.

In some embodiments, the allergic disease is selected from the group consisting of allergic lung disease, asthma, food allergy, allergen-induced airway hyperresponsiveness, allergen-induced inflammation, rhinitis, allergic rhinitis, eosinophilic esophagitis, chronic urticaria, atopic dermatitis, occupational allergy, allergic conjunctivitis, hay fever, airborne allergic sensitivities, stinging insect allergy, hypersensitivity pneumonitis, eosinophilic lung diseases, inflammatory bowel disease, ulcerative colitis, and Crohn's disease. In some embodiments, the allergic disease is allergic lung disease. In some embodiments, the allergic disease is asthma.

In some embodiments, the GLP-1R agonist is selected from the group consisting of a polypeptide, an antibody, a nucleic acid, an aptamer, or a small molecule. In some embodiments, the GLP-1R agonist is a poly peptide. In some embodiments, the GLP-1R agonist is selected from the group consisting of liraglutide, exenatide, lixisenatide, albiglutide, dulaglutide, semaglutide, and taspoglutide. In some embodiments, the GLP-1R agonist is liraglutide.

In some embodiments, the subject is a human.

In some aspects, disclosed herein is a method of treating or preventing allergic lung disease in a subject who has, or is at risk of developing an allergic lung disease, comprising administering to the subject a therapeutically effective amount of a glucagon-like peptide-1 receptor (GLP-1R) agonist.

In some aspects, disclosed herein is a method for treating or preventing an interleukin-33 (IL-33) mediated disease or disorder in a subject, the method comprising: administering to the subject a therapeutically effective amount of a glucagon-like peptide-1 receptor (GLP-1R) agonist.

In some embodiments, the interleukin-33 (IL-33) mediated disease or disorder selected from any inflammatory disease or disorder such as, but not limited to, asthma, allergy, allergic rhinitis, allergic airway inflammation, atopic dermatitis (AD), chronic obstructive pulmonary disease (COPD), respiratory syncytial virus (RSV) infection, inflammatory bowel disease (IBD), multiple sclerosis, arthritis, psoriasis, eosinophilic esophagitis, eosinophilic pneumonia, eosinophilic psoriasis, hypereosinophilic syndrome, graft-versus-host disease, uveitis, cardiovascular disease, pain, multiple sclerosis, lupus, vasculitis, chronic idiopathic urticaria and Eosinophilic Granulomatosis with Polyangiitis (Churg-Strauss Syndrome).

In some aspects, disclosed herein is a method of treating or preventing a respiratory syncytial virus (RSV) infection in a subject in need thereof, comprising administering to the subject a therapeutically effective amount of a glucagon-like peptide-1 receptor (GLP-1R) agonist.

In some embodiments, the subject is at risk for a respiratory syncytial virus (RSV) infection.

BRIEF DESCRIPTION OF THE DRAWINGS

The accompanying figures, which are incorporated in and constitute a part of this specification, illustrate several aspects described below.

Lung mRNA RSV M protein expression normalized to GAPDH. (F) ELISA for IFN-γ in whole lung homogenate (right lung only). (G) Phenome-wide association study (PheWAS) plot for THADA rs7578597 using logistic regression assuming an additive genetic model adjusted for age, sex, study site, and the first 3 principal components. rs7578597 associated with acute bronchiolitis (OR=1.24, P=$6.3 \times 10^{-3}$). Data plotted as mean+SEM. n=3-6 mice per group representative of 2 independent experiments (A-F). *p<0.05, p<0.01, *p<0.001 by one-way (A-B, D, & F) or two-way (E) ANOVA. NS=not significant.

Figure 9:
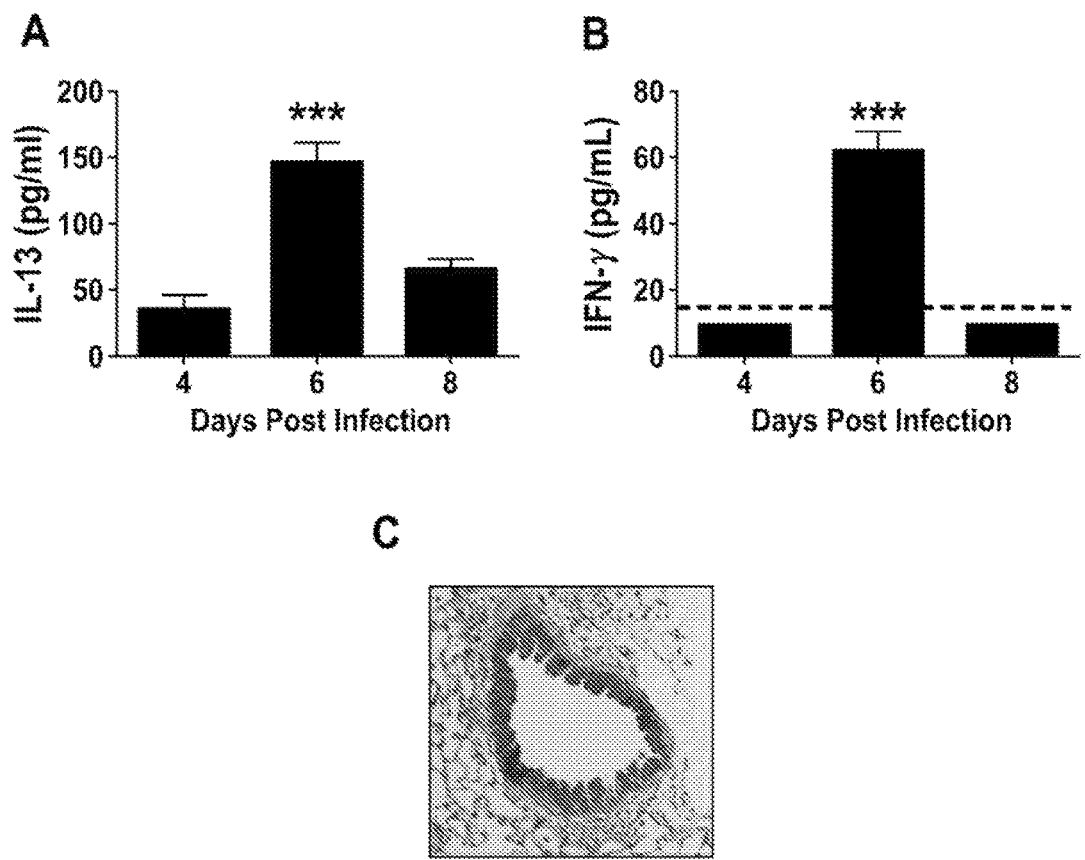

FIG. 9. RSV 12/12-6 induces lung IL-13 and mucus production. BALB/cJ mice were infected with $9 \times 10^5$ PFU of RSV strain 12/12-6. ELISA for (A) IL-13 and (B) IFN-γ in the whole lung homogenate (both lungs) 6 days after infection. (C) Representative PAS-stained section of mucus-containing airway in the lungs 8 days after infection. Data plotted as mean+SEM. n=5 mice per group. ***p<0.001 by one-way ANOVA. Dashed line is the limit of detection of the assay.

Figure 10:
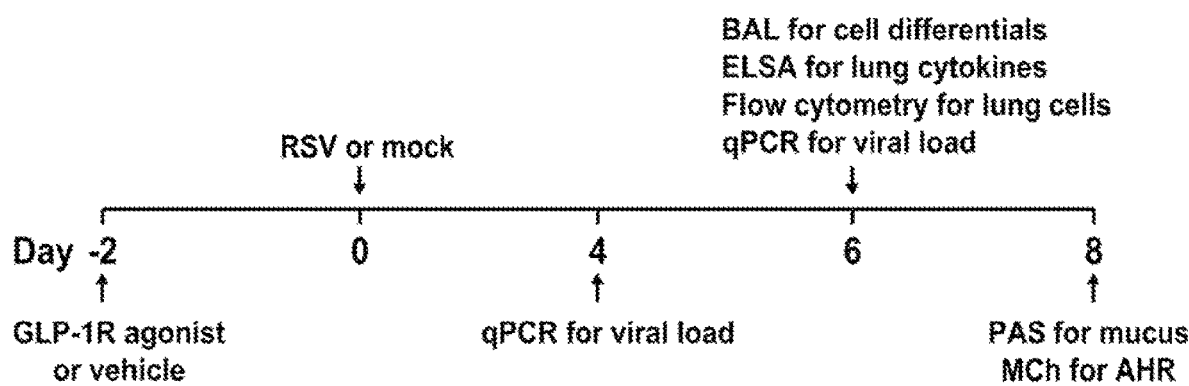

FIG. 10. Protocol for in vivo administration of GLP-1R agonist or vehicle and subsequent infection with RSV or mock preparation. Treatment with the GLP-1R agonist liraglutide or vehicle (0.1% BSA in PBS) was initiated in BALB/cJ mice on day −2. Mice were infected with $9 \times 10^5$ PFU of RSV strain 12/12-6 or mock inoculum on day 0. Treatment was given twice daily until the mice were euthanized.

Figure 11:
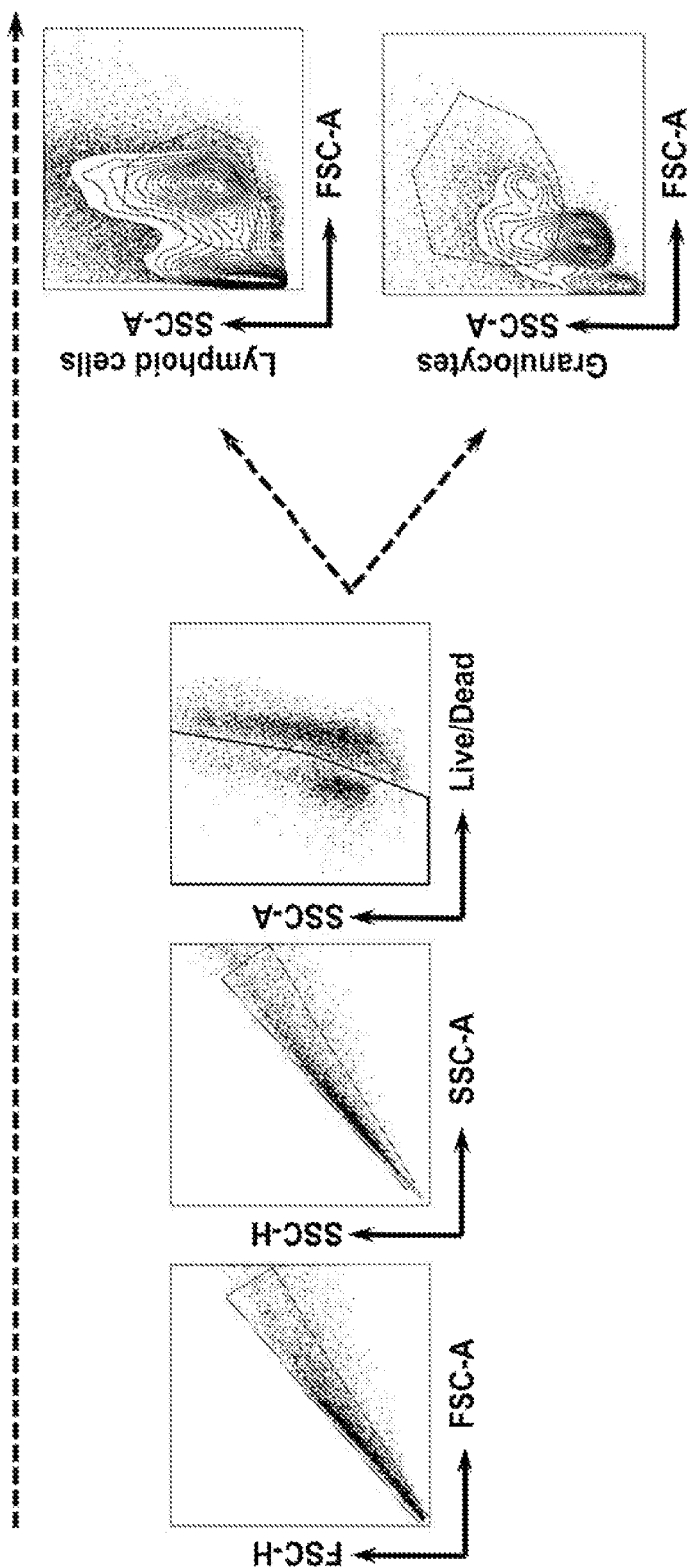
Figure 11:
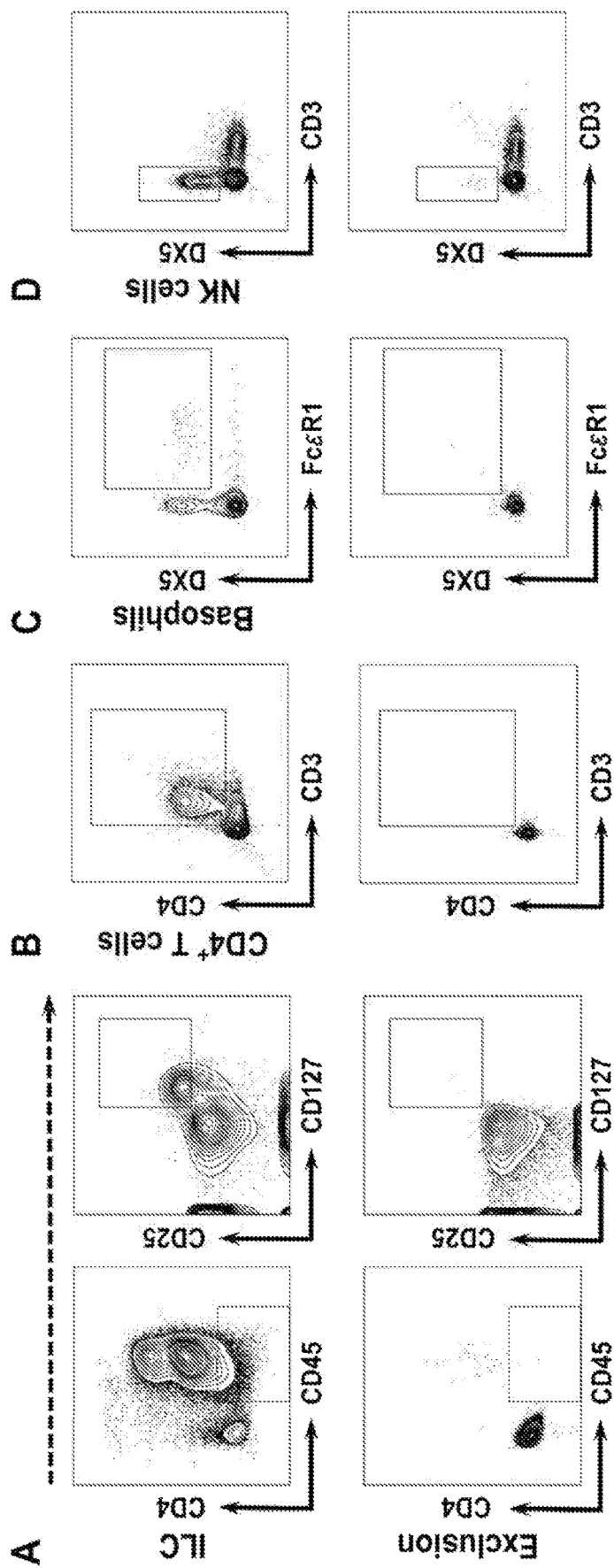
Figure 11:
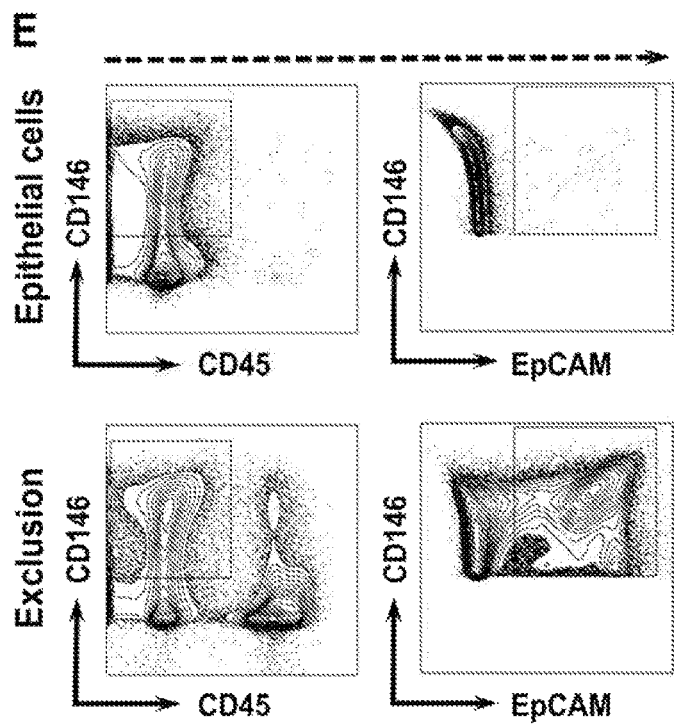

FIG. 11. GLP-1R agonist decreases RSV-induced whole lung IL-13 accumulation and airway mucus production. BALB/cJ mice were treated with GLP-1R agonist or vehicle and infected with $9 \times 10^5$ PFU of RSV strain 12/12-6 or mock inoculum. (A) Protocol for in vivo administration of GLP-1R agonist or vehicle and simultaneous infection with RSV or mock preparation. (B) ELISA for IL-13 in whole lung homogenate 6 days after infection. (C) Quantification of airway mucus in the lungs 8 days post-infection. Data plotted as mean+SEM. n=5 mice per group. *p<0.05 by unpaired t-test.

Figure 12:
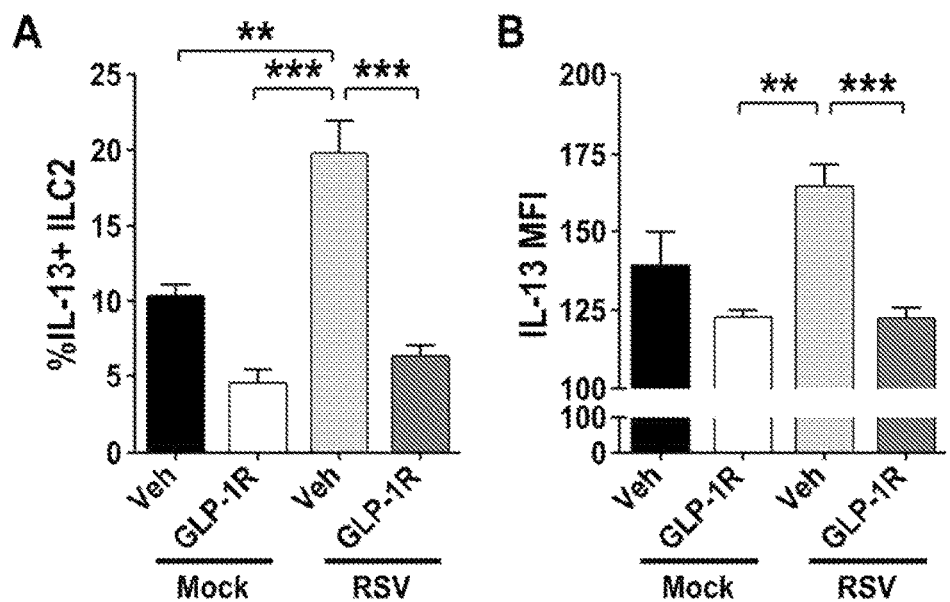
Figure 12:
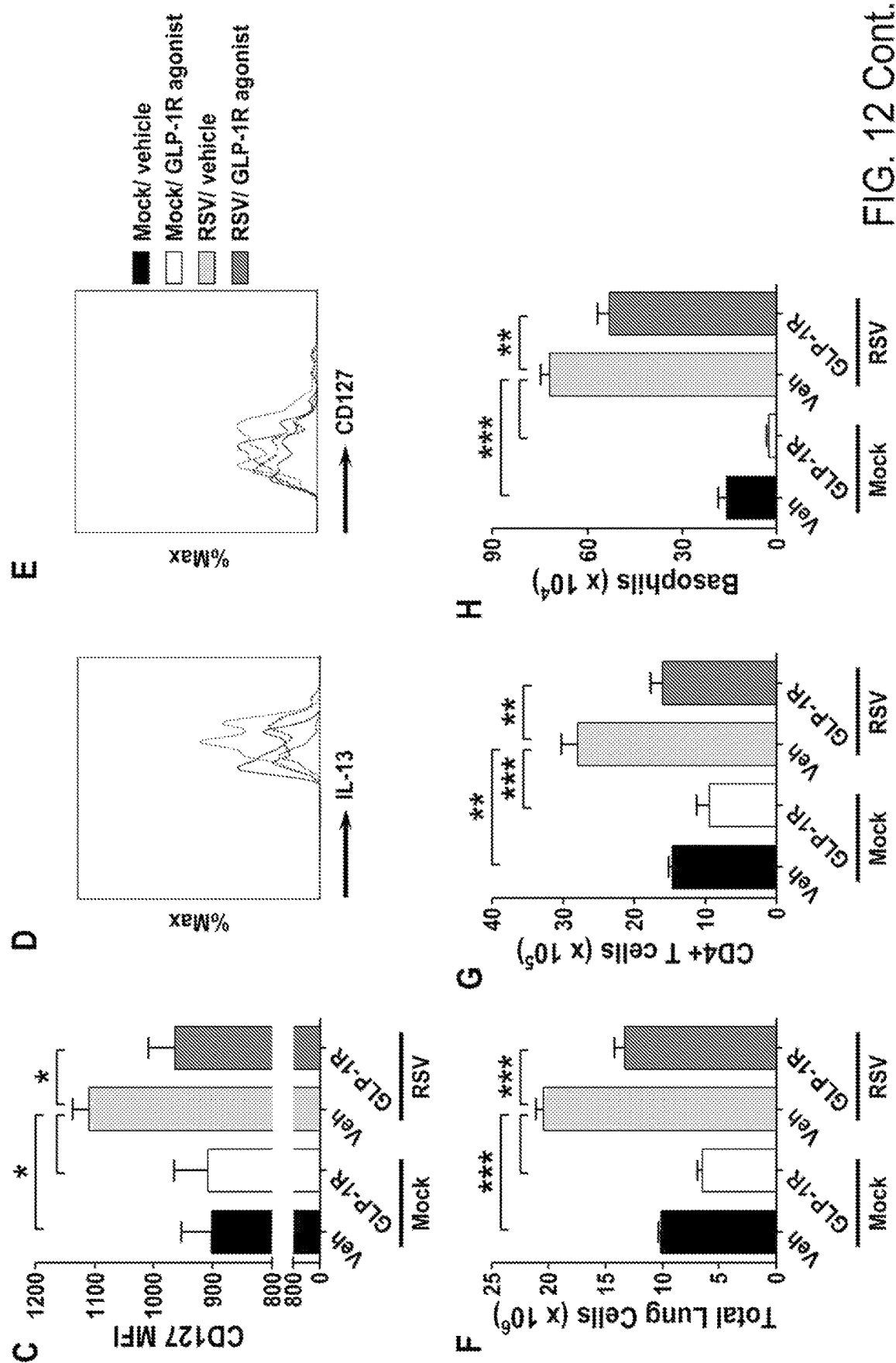

FIG. 12. Flow gating for ILC, CD4+ T cells, NK cells, basophils, and epithelial cells. (A) ILC were defined as viable Lin− CD45+ CD25+ CD127+ cells. (B) CD4+ T cells were defined as viable CD3+ CD4+ cells. (C) Basophils were defined as viable FcεRI+DX5+ cells. (D) NK cells were defined as viable DX5+ CD3− cells. (E) Epithelial cells were defined as viable CD45− CD146+ EpCAM+ cells.

Figure 13:
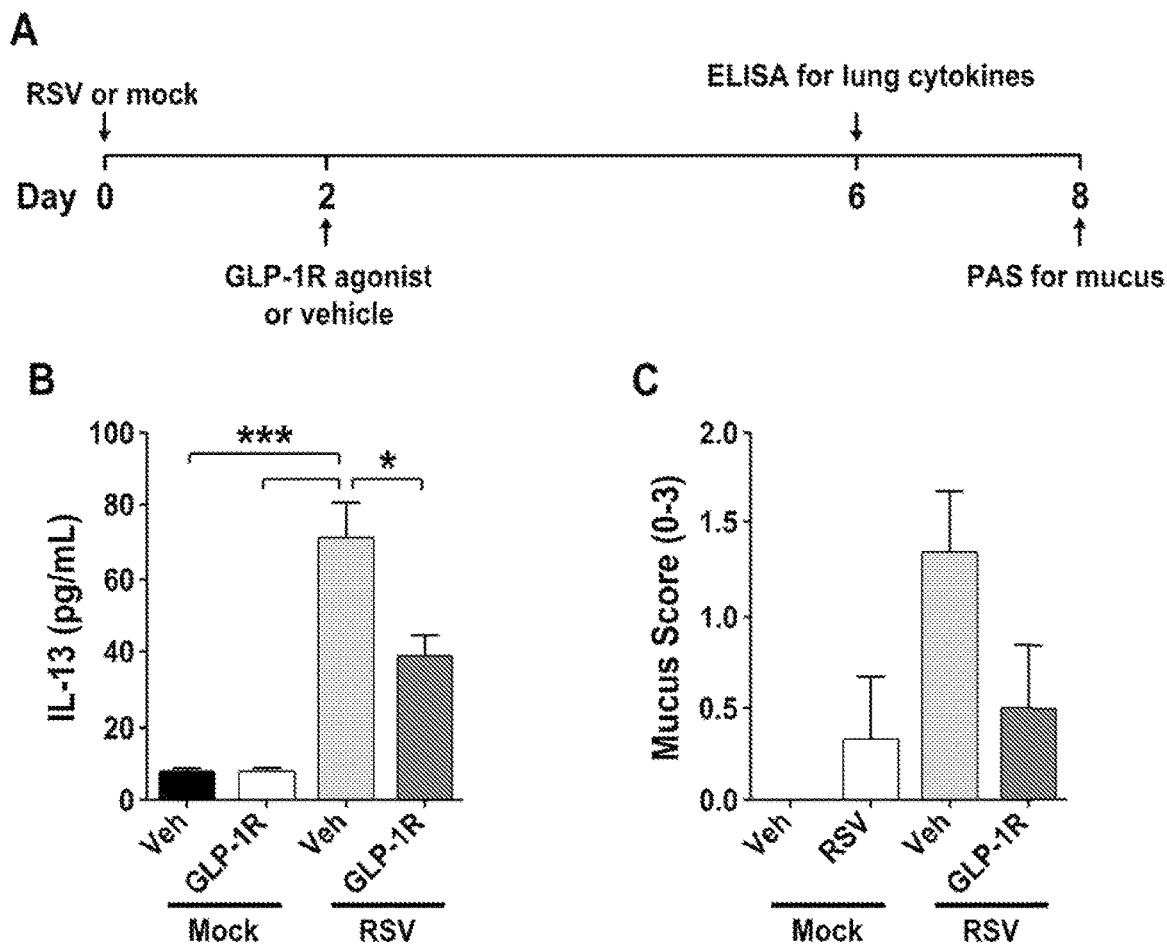

FIG. 13. GLP-1R agonist decreases IL-13-producing ILC2, Th2 cells, and basophils 6 days after RSV infection. BALB/cJ mice were treated with GLP-1R agonist or vehicle and infected with $9 \times 10^5$ PFU of RSV strain 12/12-6 or mock inoculum. (A) Percent of ILC that are IL-13+. MFI of (B) IL-13 and (C) CD127 staining in ILC2. Representative MFI of (D) IL-13 and (E) CD127 staining in ILC2 by flow cytometry. (F) Total number of live lung cells, (G) CD4+ Th2 cells, and (H) basophils. Data plotted as mean+SEM. n=3-6 mice per group representative of 2 independent experiments. *p<0.05, p<0.01, *p<0.001 by one-way ANOVA.

Figure 14:
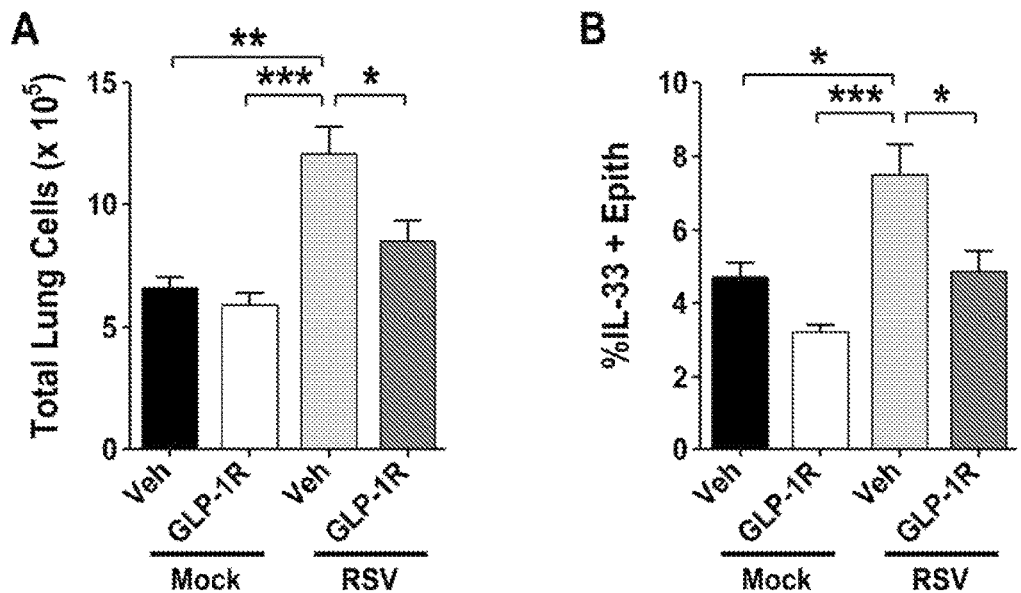

FIG. 14. GLP-1R agonist decreases whole lung IL-33 protein expression and IL-33-expressing epithelial cells 12 hours after RSV infection. Il33Citrine/+ reporter mice were treated with GLP-1R agonist or vehicle and infected with $9 \times 10^5$ PFU of RSV strain 12/12-6 or mock inoculum. (A) Total number of live lung cells and (B) percent of epithelial cells that are IL-33+. Data plotted as mean+SEM. n=3-6 mice per group representative of 2 independent experiments. *p<0.05, p<0.01, *p<0.001 by one-way ANOVA.

Figure 15:
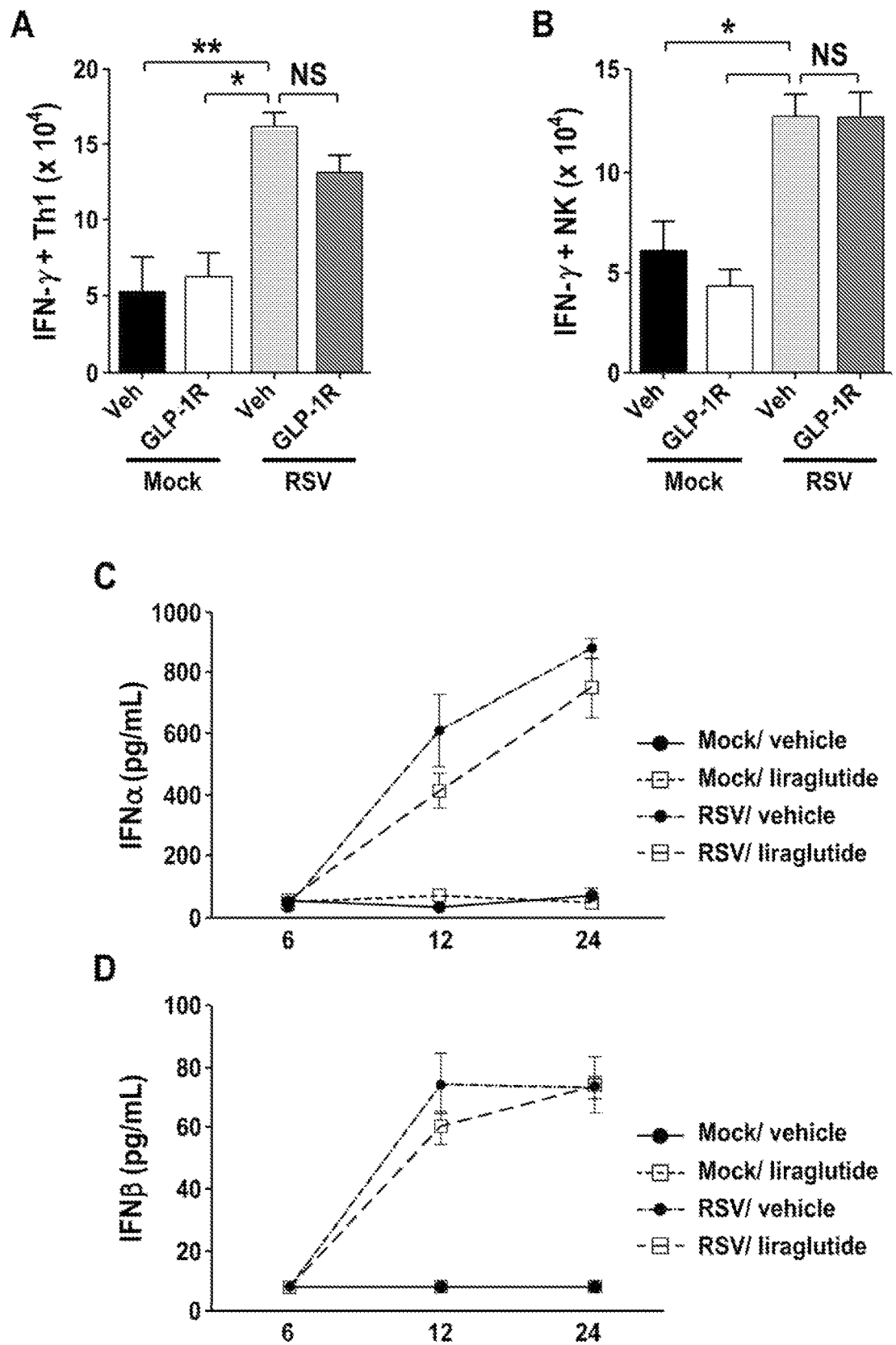
Figure 15:
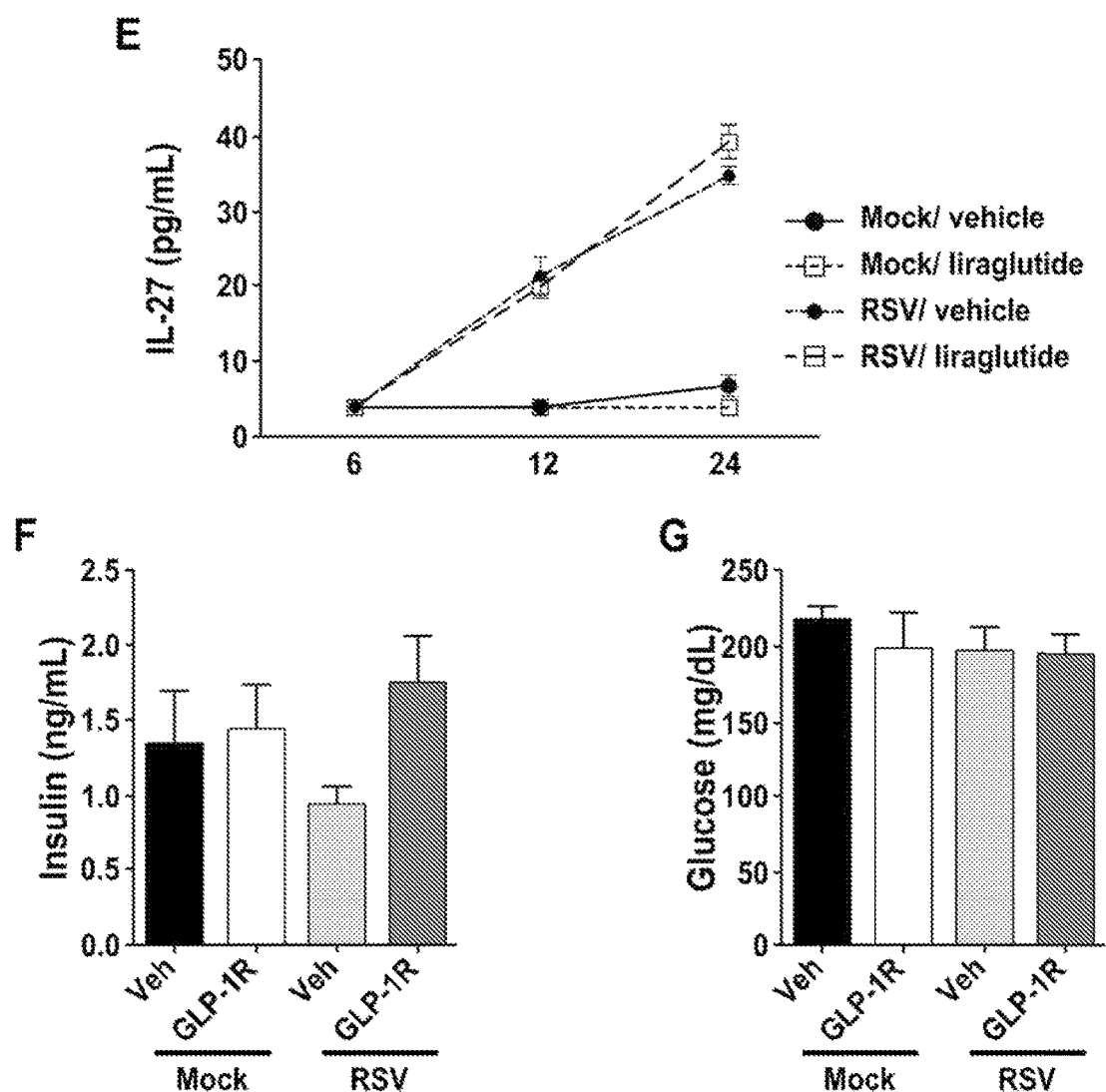

FIG. 15. GLP-1R agonist does not decrease interferon responses during RSV infection. BALB/cJ mice were treated with GLP-1R agonist or vehicle and infected with $9 \times 10^5$ PFU of RSV strain 12/12-6 or mock inoculum. (A) Total number of IFN-γ+ Th1 and (B) IFN-γ+ NK cells 6 days after infection. ELISAs for (C) IFN-α, (D) IFN-β, and (E) IL-27 in whole lung homogenate 12 hours after infection. Serum (F) insulin and (G) glucose 6 days after infection. Data plotted as mean+SEM. n=3-6 mice per group representative of 3 (A-E) or 1 (F-G) experiments. *p<0.05 and **p<0.01 by one-way (A-B & F-G) or two-way (C-E) ANOVA. NS=not significant.

Figure 16:
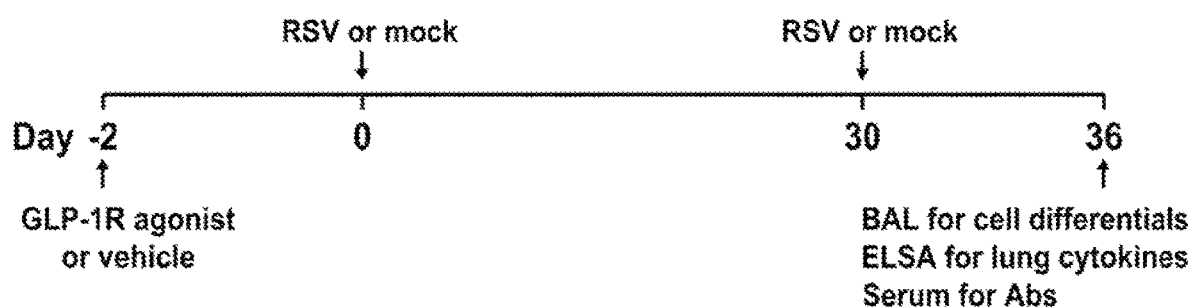

FIG. 16. Protocol for administration of GLP-1R agonist or vehicle, primary RSV or mock infection, and subsequent secondary RSV or mock infection. BALB/cJ mice were treated with GLP-1R agonist or vehicle beginning on day −2 and infected with $9 \times 10^5$ PFU of RSV strain 12/12-6 or mock inoculum on day 0. Treatment was given twice daily until day 8. On day 30, mice were infected a second time with $9 \times 10^5$ PFU of RSV strain 12/12-6 or mock inoculum.

Figure 17:
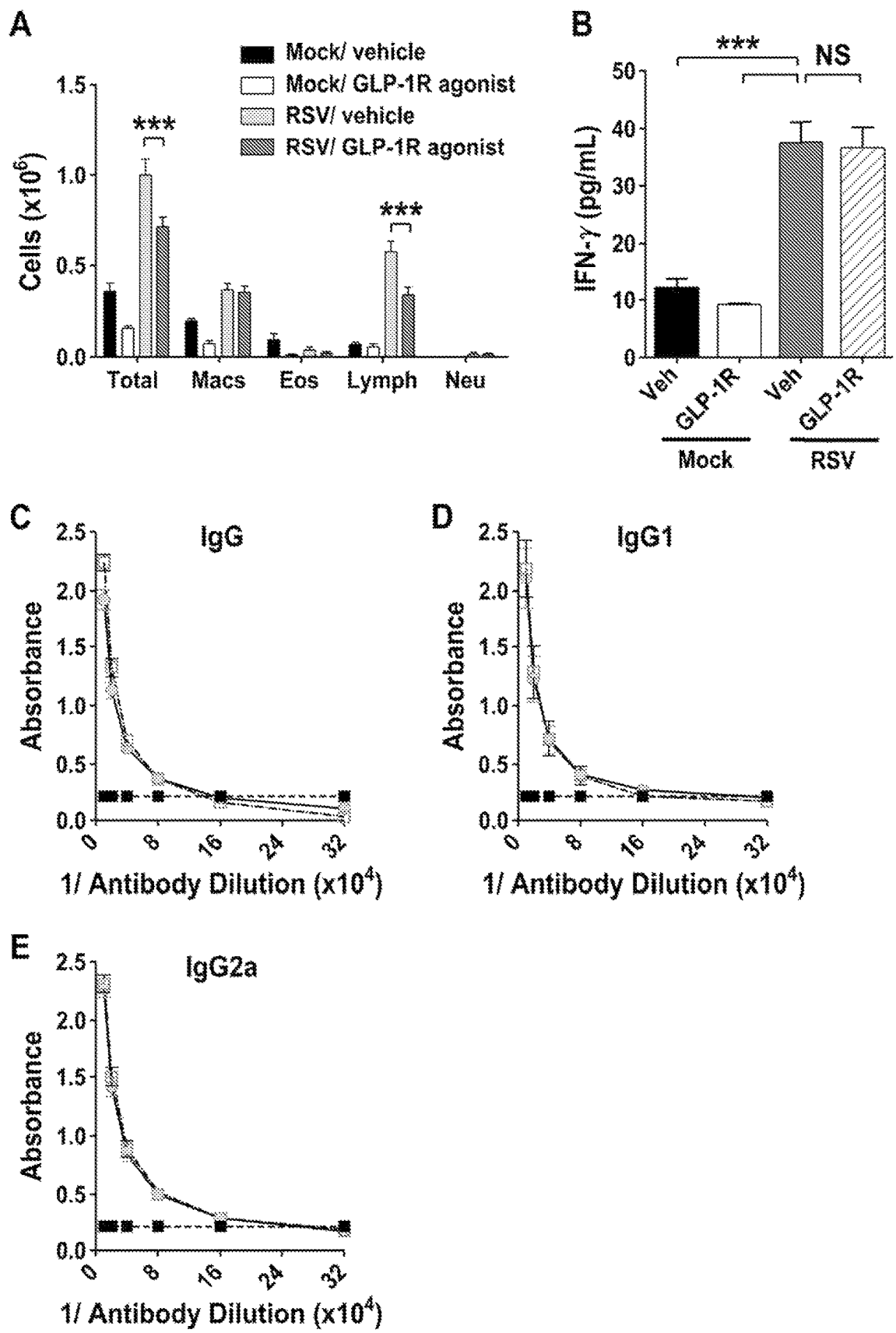

FIG. 17. GLP-1R agonist treatment during primary infection prevents airway inflammation and does not reduce anti-RSV antibody responses or lung IFN-γ protein expression during secondary RSV infection. BALB/cJ mice were treated with GLP-1R agonist or vehicle and infected with $9 \times 10^5$ PFU of RSV strain 12/12-6 or mock inoculum. Mice were re-infected 30 days after primary infection, and serum was collected 6 days after secondary infection. (A) BAL cell counts 6 days post-infection. (B) ELISA for IFN-γ in whole lung homogenate (right lung only). ELISA for RSV F-protein-specific (C) IgG, (D) IgG1, and (E) IgG2a. Data plotted as mean+SEM. n=6-12 mice per group combined from 2 independent experiments. One-way ANOVA. NS=not significant.

DETAILED DESCRIPTION

Disclosed herein are methods of treating allergic disorders and respiratory syncytial virus (RSV) infections with a GLP-1R agonist. The inventors found that GLP-1R agonists inhibited IL-33 expression and release from the lungs of mice in response to an airway challenge the allergen extract of the aeroallergen *Alternaria alternata*, an aeroallergen which has protease activity and which is associated with severe asthma exacerbations. This is the first study to identify an FDA approved pharmacologic agent that inhibits lung IL-33 release, providing an alternative to biologic therapies that target IL-33-mediated diseases.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

The following definitions are provided for the full understanding of terms used in this specification.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

Methods

In some aspects, disclosed herein is a method of treating or preventing an allergic disease in a subject who has, or is at risk of developing an allergic disease, comprising administering to the subject a therapeutically effective amount of a glucagon-like peptide-1 receptor (GLP-1R) agonist.

In some embodiments, the allergic disease is selected from the group consisting of allergic lung disease, asthma, food allergy, allergen-induced airway hyperresponsiveness, allergen-induced inflammation, rhinnis, allergic rhinitis, eosinophilic esophagitis, chronic urticaria, atopic dermatitis, occupational allergy, allergic conjunctivitis, hay fever, airborne allergic sensitivities, stinging insect allergy, hypersensitivity pneumonitis, eosinophilic lung diseases, inflammatory bowel disease, ulcerative colitis, and Crohn's disease. In some embodiments, the allergic disease is allergic lung disease. In some embodiments, the allergic disease is asthma.

In some embodiments, the allergic disease is selected from the group consisting of allergic sinusitis, anaphylactic syndrome, angioedema, allergic contact dermatitis, erythema nodosum, and erythema multiforme.

In some embodiments, the GLP-1R agonist is selected from the group consisting of a polypeptide, an antibody, a nucleic acid, an aptamer, or a small molecule. In some embodiments, the GLP-1R agonist is a polypeptide. In some embodiments, the GLP-1R agonist is selected from the group consisting of liraglutide, exenatide, lixisenatide, albiglutide, dulaglutide, semaglutide, and taspoglutide. In some embodiments, the GLP-1R agonist is liraglutide.

In some embodiments, the subject is a human.

In some aspects, disclosed herein is a method of treating or preventing allergic lung disease in a subject who has, or is at risk of developing an allergic lung disease, comprising administering, to the subject a therapeutically effective amount of a glucagon-like peptide-1 receptor (GLP-1R) agonist.

In some embodiments, the GLP-1R agonist is selected from the group consisting of a polypeptide, an antibody, a nucleic acid, an aptamer, or a small molecule. In some embodiments, the GLP-1R agonist is selected from the group consisting of liraglutide, exenatide, lixisenatide, albiglutide, dulaglutide, semaglutide, and taspoglutide. In some embodiments, the GLP-1R agonist is liraglutide.

In some embodiments, the subject is a human.

In some aspects, disclosed herein is a method of treating or preventing an allergic disease in a subject, comprising administering to the subject a therapeutically effective amount of a glucagon-like peptide-1 receptor (GLP-1R) agonist.

In some aspects, disclosed herein is a method for treating or preventing an interleukin-33 (IL-33) mediated disease or disorder in a subject, the method comprising: administering to the subject a therapeutically effective amount of a glucagon-like peptide-1 receptor (GLP-1R) agonist.

As used herein the term "IL-33 mediated disease or disorder" may be selected from any inflammatory disease or disorder such as, but not limited to, asthma, allergy, allergic rhinitis, allergic airway inflammation, atopic dermatitis (AD), chronic obstructive pulmonary disease (COPD), respiratory syncytial virus (RSV) infection, inflammatory bowel disease (IBD), multiple sclerosis, arthritis, psoriasis, eosinophilic esophagitis, eosinophilic pneumonia, eosinophilic psoriasis, hypereosinophilic syndrome, graft-versus-host disease, uveitis, cardiovascular disease, pain, multiple sclerosis, lupus, vasculitis, chronic idiopathic urticaria, and Eosinophilic Granulomatosis with Polyangiitis (Churg-Strauss Syndrome).

The asthma may be selected from the group consisting of allergic asthma, non-allergic asthma, severe refractory asthma, asthma exacerbations, viral-induced asthma or viral-induced asthma exacerbations, steroid resistant asthma, steroid sensitive asthma, eosinophilic asthma or non-eosinophilic asthma and other related disorders characterized by airway inflammation or airway hyperresponsiveness (AHR).

The COPD may be a disease or disorder associated in part with, or caused by, cigarette smoke, air pollution, occupational chemicals, allergy or airway hyperresponsiveness.

The allergy may be associated with foods, pollen, mold, dust mites, animals, or animal dander. In some embodiments, the allergy of the allergic reaction is a food allergy. In some embodiments, the food allergy is a nut allergy, peanut allergy, shellfish allergy, fish allergy, milk allergy, egg allergy, wheat allergy, or soybean allergy.

The IBD may be selected from the group consisting of ulcerative colitis, Crohn's Disease, collagenous colitis, lymphocytic colitis, ischemic colitis, diversion colitis, Behcet's syndrome, infective colitis, indeterminate colitis, and other disorders characterized by inflammation of the mucosal layer of the large intestine or colon.

The arthritis may be selected from the group consisting of osteoarthritis, rheumatoid arthritis and psoriatic arthritis.

In some embodiments, the GLP-1R agonist is selected from the group consisting of a polypeptide, an antibody, a nucleic acid, an aptamer, or a small molecule. In some embodiments, the GLP-1R agonist is selected from the group consisting of liraglutide, exenatide, lixisenatide, albiglutide, dulaglutide, semagiutide, and taspoglutide. In some embodiments, the GLP-1R agonist is liraglutide.

In some embodiments, the subject is a human.

In some embodiments, the administration of the GLP-1R agonist decreases IL33 expression (mRNA and/or protein expression).

In some embodiments, administration of the GLP-1R agonist reduces group 2 innate lymphoid cell (ILC2) cytokine production. In some embodiments, administration of the GLP-1R agonist reduces IL-5 and/or IL-13 production from lung ILC2. In some embodiments, administration of the GLP-1R agonist reduces the number of lung epithelial cells expressing IL-33 and/or the level of IL-33 expression by individual cells. In some embodiments, administration of the GLP-1R agonist reduces lung DUOX1 mRNA expression. In some embodiments, administration of the GLP-1R agonist suppresses the number of total, IL-5$^+$, and IL-13$^+$ lung ILC2. In some embodiments, administration of the GLP-1R agonist decreases IL-5, IL-13, CCL17, CCL 22 and/or CCL24 expression. In some embodiments, administration of the GLP-1R agonist decreases protein level of IL-13. In some embodiments, administration of the GLP-1R agonist suppresses/decreases IL-33 release and inhibits ILC2-dependent innate type 2 airway inflammation.

In some aspects, disclosed herein is a method of treating or preventing a respiratory syncytial virus (RSV) infection in a subject in need thereof, comprising administering to the subject a therapeutically effective amount of a glucagon-like peptide-1 receptor (GLP-1R) agonist.

In some embodiments, the GLP-1R agonist is selected from the group consisting of a polypeptide, an antibody, a nucleic acid, an aptamer, or a small molecule. In some embodiments, the GLP-1R agonist is selected from the group consisting of liraglutide, exenatide, lixisenatide, albiglutide, dulaglutide, semaglutide, and taspoglutide. In some embodiments, the GLP-1R agonist is liraglutide.

In some embodiments, the subject is a human. In some embodiments, the subject at risk for a respiratory syncytial virus (RSV) infection.

In some embodiments, administration of the GLP-1R agonist deceases the total number of group 2 innate lymphoid cells (ILC2). In some embodiments, administration of the GLP-1R agonist decreases the percentage of ILC that were IL-13$^+$ compared to RSV-infected vehicle-treated mice. In some embodiments, administration of the GLP-1R agonist decreases the numbers of total bronchoalveolar lavage (BAL) cells and lymphocytes compared to RSV-infected vehicle-treated mice. In some embodiments, administration of the GLP-1R agonist inhibits the expression of IL-33 by epithelial cells during RSV infection.

GLP-1R Agonists

In some embodiments, the GLP-1R agonist is selected from the group consisting of a polypeptide, an antibody, a nucleic acid, an aptamer, or a small molecule. In some embodiments, the GLP-1R agonist is selected from the group consisting of liraglutide, exenatide, lixisenatide, albiglutide, dulaglutide, semaglutide, and taspoglutide. In some embodiments, the GLP-1R agonist is liraglutide.

In some embodiments, the GLP-1R agonist can be a polypeptide. For example, polypeptides include GLP-1 (7-36), GLP-1 (7-37) or GLP-1 (1-37), or variants thereof. See, for example, U.S. Pat. No. 8,758,761, which is incorporated by reference in its entirety. GLP-1 is rapidly metabolized by a peptidase (dipeptidylpeptidase IV or DPP-IV). One way to counter the rapid degradation is to couple it to a fatty acid. Liraglutide is such a preparation. Liraglutide binds to serum albumin and is a poor substrate for the peptidase. In some embodiments, single injections of liraglutide give therapeutically active blood levels for 8 to 15 hours.

In addition, WO2007113205 and WO2006097538 also disclose a series of GLP-1 analogues or derivatives thereof produced by chemical modification or amino acid substitution, in which the most representative one is liraglutide. Liraglutide is a derivative of GLP-1, whose structure contains a. GLP-1 analogue of which the sequence is 97% homologous with human GLP-1, and this GLP-1 analogue is linked with palmitic acid covalently to form liraglutide. The palmitic acid in the structure will form a certain steric hindrance to prevent the degradation by DPP-1V and to reduce renal clearance. Because of the characteristics described above, the half-life of Liraglutide in the human body administered by subcutaneous injection is about 10-14 hours. In some embodiments, it can be administered once on day and the daily dose is 0.6-1.8 mg.

Exenatide is a synthetic Exendin-4, with the trade name Byetta®. Exenatide has been approved for the treatment of Type 2 diabetes mellitus (T2DM) by the FDA. It has 50% homology with mammalian GLP-1 in sequence and has a similar affinity site of the receptor with GLP-1. (See Drucker D J, Nauck M A. The incretin system: glucagon-like peptide-1 receptor agonists and dipeptidyl peptidase-4 inhibitors in type 2 diabetes. Lancet. 2006, 368(9548):1696-1705). Exendin-4 has a longer half-life than GLP-1 and has recently been shown to have a hypoglycemic effect in humans when given twice a day for one month. Exenatide is a 39-amino acid peptide which closely resembles exendin-4. It is DPP-4 resistant and has many of the actions of GLP-1.

In some embodiments, the GLP-1R agonist can be a GLP-1 analogue. See, for example, U.S. Pat. No. 8,614,182, which is incorporated by reference in its entirety.

Compositions

Compositions, as described herein, comprising an active compound and an excipient of some sort may be useful in a variety of applications.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, varoius gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Glucagon-Like Peptide 1 Signaling Inhibits Allergen-Induced Lung IL-33 Release and Reduces Group 2 Innate Lymphoid Cell (ILC2) Cytokine Production In Vivo

BACKGROUND

IL-33 is one of the most consistently associated gene candidates for asthma identified by genome wide association studies (GWAS) in diverse ethnic groups.[1-4] IL-33 is predominantly produced by epithelial cells in response to protease containing aeroallergens and its release is mediated by dual oxidase 1 (DUOX1).[5] IL-33 activates group 2 innate lymphoid cells (ILC2) to produce the type 2 cytokines IL-5 and IL-13 that initiate innate immunity-driven allergic responses.[6,7] In addition, IL-33 polarizes naïve CD4 T cells to differentiate into effector T helper 2 (Th2) cells, which produce IL-4, IL-5, and IL-13 that are responsible for adaptive immunity-mediated allergen-induced responses.[8] Therefore, IL-33 is a central mediator of both innate and adaptive immunity regulated allergic inflammation in the lung that have a role in the pathogenesis of conditions such as asthma, and IL-33 has been deemed to be an important therapeutic target in inhibiting allergic diseases.[9] However, there have been no reports identifying pharmacologic agents which inhibit lung IL-33 protein release or expression.

Glucagon-like peptide-1 (GLP-1) is a peptide hormone synthesized and released by enteroendocrine L-cells in the ileum and large intestine following oral food intake.[10] GLP-1 has a role in glycemic control by inducing glucose-dependent insulin secretion from β-cells and inhibiting glucagon release from α-cells in the pancreas.[11,12] GLP-1 also induces weight loss by promoting satiety.[13] GLP-1 receptor (GLP-1R) agonists, such as liraglutide and exenatide are approved by the Food and Drug Administration (FDA) for treatment of type 2 diabetes (T2D).[14, 15] Several studies report that GLP-1R agonists had anti-inflammatory effects in multiple disorders including T2D. For instance, GLP-1R agonist administration decreased TNFα and IL-6 production by peripheral blood mononuclear cells (PBMC) of obese patients with T2D[16] and diabetic mouse adipose tissue.[17] In addition, the GLP-1R agonist, exendin-4, reduced serum inflammatory cytokines during LPS-induced endotoxemia,[18] liver inflammation, and aortic atherosclerosis in a rodent model.[19] These data indicate that GLP-1R agonists down-regulate innate inflammatory responses to endotoxins or endogenous inflammatory mediators. Further, it has been reported that liraglutide attenuated bleomycin-induced pulmonary fibrosis[20] and OVA-induced chronic airway inflammation.[21] However, no studies have reported the effect of GLP-1R agonists on lung IL-33 expression or release, or the effect of GLP-1R agonists on the innate allergic inflammatory response that is mediated by ILC2.

In this example, it was found that the GLP-1R agonist, liraglutide, inhibited IL-33 expression and release from the lungs of mice in response to an airway challenge the allergen extract of the aeroallergen *Alternaria alternata*, an aeroallergen which has protease activity and which is associated with severe asthma exacerbations.[22, 23] Further, GLP-1R agonist treatment inhibited lung DUOX1 expression, providing a potential mechanism by which GLP-1R signaling inhibits lung IL-33 release in response to aeroallergen challenge. In addition, GLP-1R agonist treatment inhibited *Alternaria* extract-induced IL-5 and IL-13 production from lung ILC2, blunted airway mucus and responsiveness, and reduced lung eosinophilia. This report is the first to identify an FDA approved pharmacologic agent that inhibits lung IL-33 release, providing an alternative to biologic therapies that target IL-33-mediated diseases.

Abbreviations Used in this Example

ILC2: group 2 innate lymphoid cells,
GLP-1: glucagon-like peptide-1,
GLP-1R: glucagon-like peptide-1 receptor,
Th2: T helper 2,
FDA: Food and Drug Administration,
T2D: type 2 diabetes,
WT: wild type,
BAL: bronchoalveolar lavage,
DUOX1: dual oxidase 1,
MFI: mean fluorescence intensity,
AR: airway responsiveness,
cAMP: cyclic adenosine monophosphate,
PKA: protein kinase A,
HBE: human bronchial epithelial cells, Methods Mice Nine- to twelve-week old female wild type (WT) BALB/c mice were obtained from Jackson Laboratories (Bar Harbor, Me.). IL-33$^{Citrine/+}$ reporter mice were generated by crossbreeding WT BALB/c mice and IL-33$^{Citrine/Citrine}$ mice that are the kind gift of Dr. Andrew N.J. McKenzie.[24] Transgenic mice expressing mApple protein under the control of the GLP-1R promoter were generated as previously described.[25] Animal experiments were approved by the Institutional Animal Care and Use Committee at Vanderbilt University, and were conducted according to the guidelines for the Care and Use of Laboratory Animals prepared by the Institute of Laboratory Animal Resources, National Research Council.

GLP-1R Agonist Treatment and *Alternaria* Extract-Challenge in Mouse Model

GLP-1R agonist, liraglutide (Novo Nordisk Inc., Bagsvaerd, Denmark) or 50 µl 0.1% BSA/PBS as vehicle was administered subcutaneously 4 h before and 4 h after *Alternaria* extract (GREER, Lenoir, N.C.), or vehicle-challenge (FIG. 2, A and FIG. 3, A) from day −2 to day 3. From day 0 to day 3, either 5 µg (protein amount) of *Alternaria* extract in 100 µl PBS or 100 µl of PBS as vehicle was used as an intranasal challenge to mice anesthetized with ketamine/xylazine. The mice were sacrificed and bronchoalveolar lavage (BAL) fluid and whole lungs were harvested 1 h after the first challenge of *Alternaria* extract or the vehicle, or 24 h or 48 h after the last challenge of *Alternaria* extract or the vehicle.

Flow Cytometry

The harvested lungs were minced and digested with collagenase IV (1 mg/ml, SIGMA-Aldrich, St. Louis, Mo.) and DNase I (50 IU/ml, SIGMA-Aldrich) in RPMI1640 with 5% FBS for 45 minutes at 37° C. and a single cell suspension was obtained by grinding and passing the digested lung through a 70 µm cell strainer. The cells were stimulated with PMA (10 ng/ml), ionomycin (1 µM) and BD GolgiStop™ (BD Biosciences, San Jose, Calif.) at the manufacturer's recommended concentration for 5 hours. Then both cell surface and intracellular cytokine staining were performed. All samples were measured on a BD LSR II Flow Cytometer and analyzed using FlowJo Software.

Cytokine Measurements

DuoSet ELISA kits (CCL11, CCL17, CCL22, CCL24, IL-4, IL-9, and IL-33) from R&D Inc. (Minneapolis, Minn.) and Ready-Set-GO!® ELISA kits (IL-5 and IL-13) from Affymetrix eBioscience (San Diego, Calif.) were used to measure the concentration of cytokines and chemokines in BAL fluids and lung homogenates according to manufacturer's instructions. Values below the detection limit were assigned a value at half of the lower limit of detection to allow for statistical analysis.

Statistical Analysis

All data were analyzed with GraphPad Prism 5 (GraphPad Software, La Jolla, Calif.). The p values were calculated by one-way analysis of variance (ANOVA) with Bonferroni-multiple pairs comparisons test. Values of p<0.05 were considered significant between two groups.

Results

GLP-1R Expression on Lung Epithelial Cells

Figure 1:
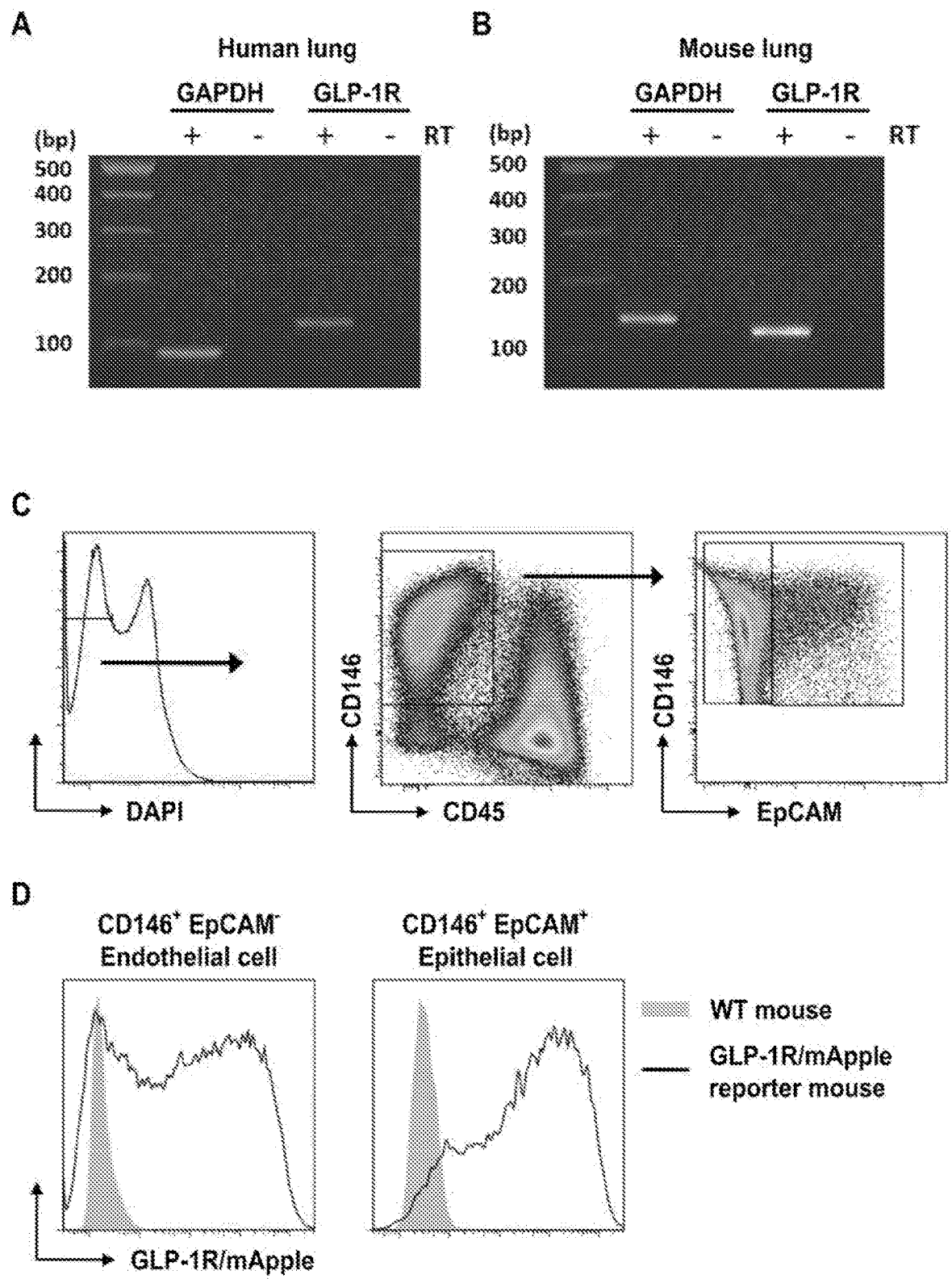
FIG. 1. GLP-1R expression on lung epithelial cells. A and B, RT-PCR of GLP-1R in (A) human lung and (B) mouse lung. Results are representative of 3 different samples. RT=reverse transcriptase. C, The gating strategy of epithelial cells and endothelial cells. D, Representative histograms of mApple (GLP-1R) expression on CD45$^-$ CD146$^+$EpCAM$^-$ endothelial cells and CD45$^-$ CD146$^+$EpCAM$^+$ epithelial cells in the lungs from WT mice (filled gray area) or GLP-1R/mApple reporter mice (black line). Results are representative of 3 different mice.

GLP-1R expression was examined on lung epithelial cells to determine whether GLP-1 could directly modulate epithelial cell function. GLP-1R mRNA expression was detected in normal human lung as well as mouse lung (FIGS. 1, A and B). Further, GLP-1R protein expression was also detected on mouse lung epithelial cells and endothelial cells (FIGS. 1, C and D) using GLP-1R/mApple reporter mice. These results provide a rationale for investigating the effect of GLP-1R signaling in response to airway *Alternaria* extract-challenge.

Figure 2:
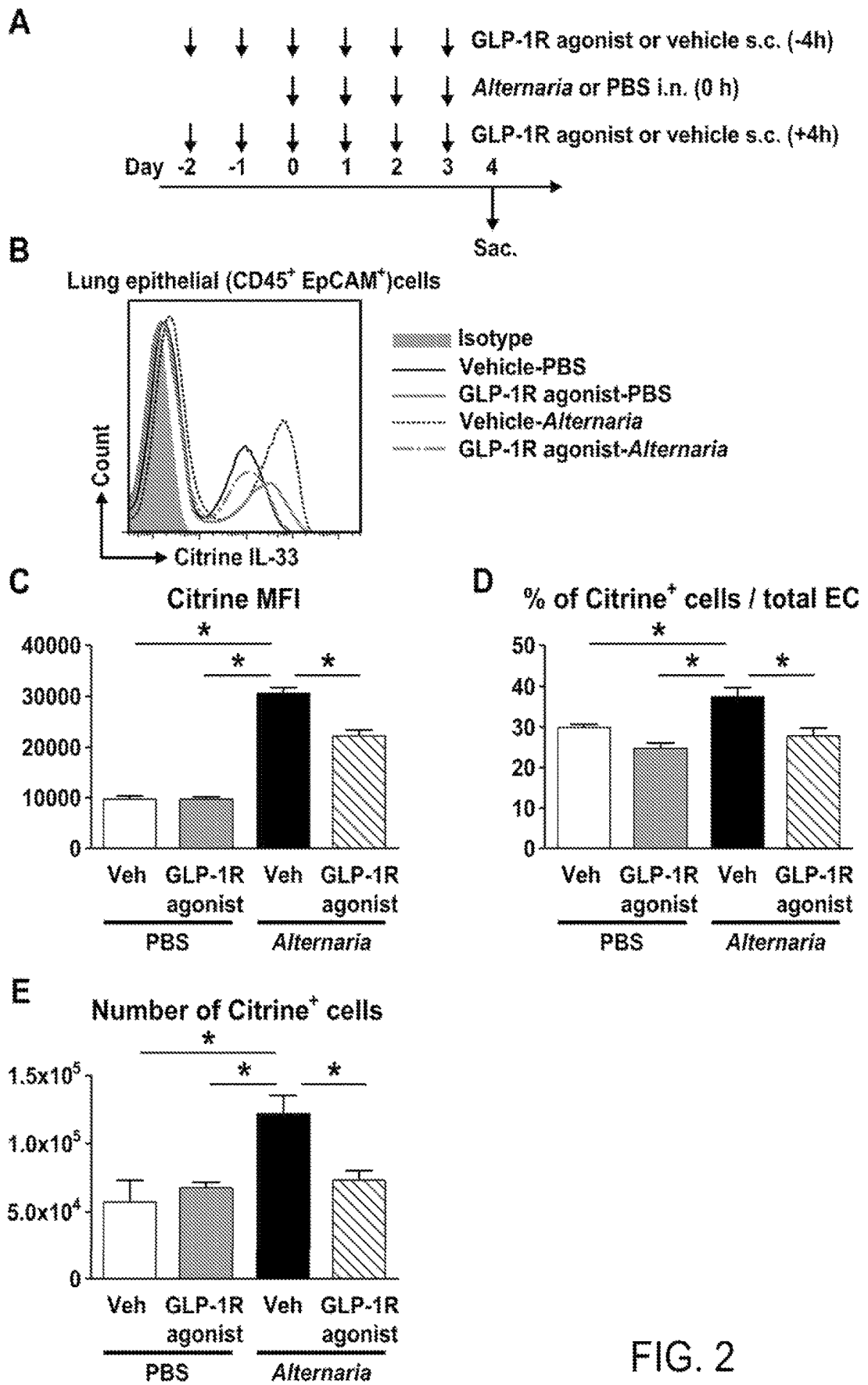
FIG. 2. GLP-1R agonist treatment suppresses *Alternaria* extract-induced IL-33 expression in lung epithelial cells. A, Mice were challenged with *Alternaria* extract intranasally for 4 consecutive days. GLP-1R agonist or its vehicle was administered subcutaneously on day −2 and −1, and then every 4 h before and after *Alternaria* extract-challenge on day 0-3. The dose of GLP-1R agonist was 0.05 mg/kg on day −2, 0.1 mg/kg on day −1, and 0.2 mg/kg on day 0-3. B, Representative histograms of citrine (IL-33) expression on CD45$^-$ EpCAM$^+$ cells in the lungs from WT mice (filled gray area) or IL-33$^{Citrine/+}$ reporter mice challenged with vehicle-PBS, GLP-1R agonist-PBS, vehicle-*Alternaria* extract, and GLP-1R agonist *Alternaria* extract. C-E, The MFI, the percentage, and the number of Citrine$^+$ CD45$^-$ EpCAM$^+$ cells in the lung. The results are representative of 2 independent experiments, and shown as mean±S.E.M. of 3 mice in PBS-challenged groups and 5 mice in *Alternaria* extract-challenged groups. Veh=vehicle. PBS=phosphate buffered saline. EC=epithelial cells *P<0.05

GLP-1R Agonist Treatment Suppresses *Alternaria* Extract-Induced IL-33 Expression in Lung Epithelial Cells IL-33 is a key activator of the innate allergic airway response, and in particular IL-33 stimulates ILC2.[6] Therefore, GLP-1R agonist treatment was tested to see if it decreases IL-33 protein expression following airway *Alternaria* extract-challenge for 4 consecutive days (FIG. 2, A). To confirm the localization of IL-33 expression and the effect of GLP-1R agonist on per cell IL-33 expression level, IL-33$^{Citrine/+}$ reporter mice were used. *Alternaria* extract-challenge significantly increased mean fluorescence intensity (MFI) of citrine fluorescence as a marker of IL-33 expression by lung epithelial cells (CD45$^-$ EpCAM$^+$), and the percentage and the number of the citrine epithelial cells. GLP-1R agonist treatment significantly decreased the *Alternaria* extract-induced MFI of citrine in the lung epithelial cells, the percentage and the number of citrine$^+$ epithelial cells compared with the vehicle treatment (FIG. 2, B-E). These results indicate that GLP-1R agonist treatment reduced the number of lung epithelial cells expressing IL-33 and the level of IL-33 expression by individual cells following *Alternaria* extract-challenge.

Figure 3:
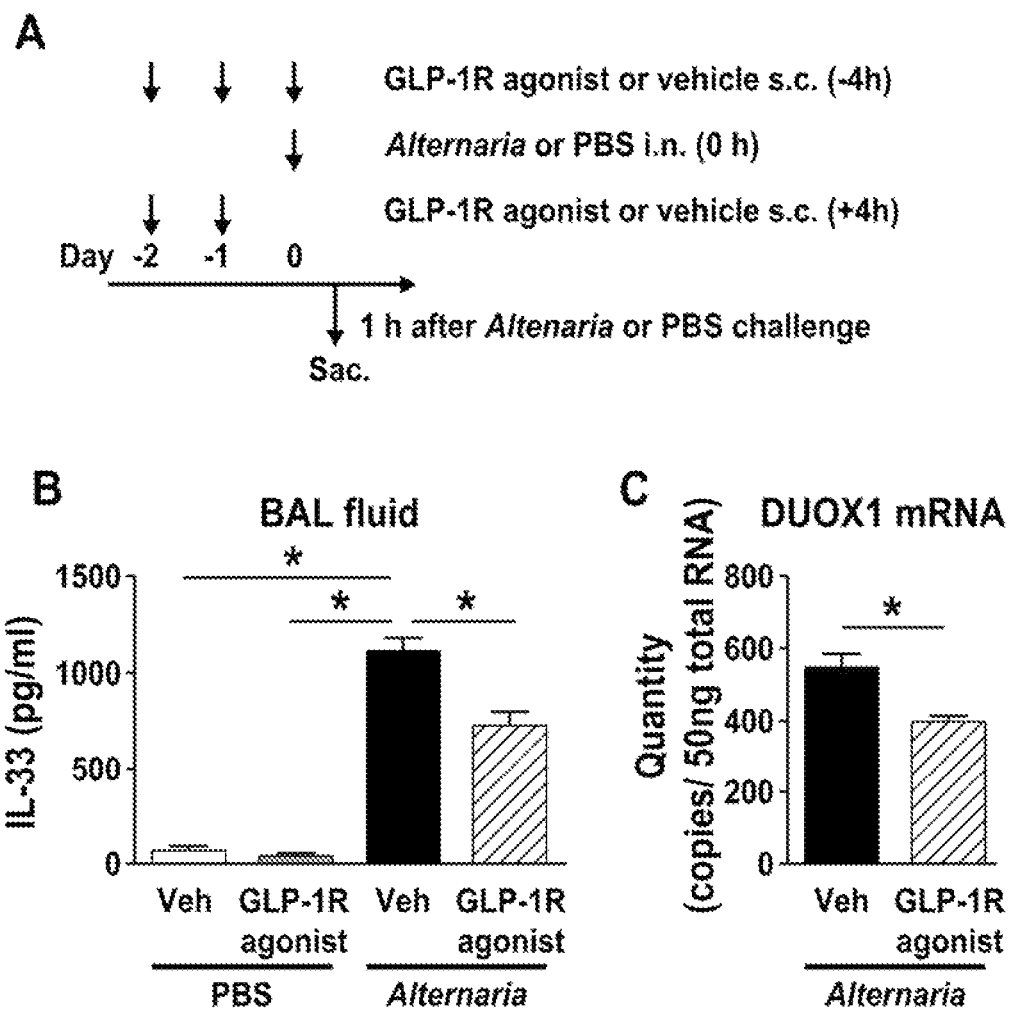
FIG. 3. GLP-1R agonist treatment suppresses *Alternaria* extract-induced IL-33 release in the BAL fluid. A, GLP-1R agonist or its vehicle was administered subcutaneously on day −2 and −1, and then 4 h before *Alternaria* extract-challenge on day 0. The dose of GLP-1R agonist was 0.05 mg/kg on day −2, 0.1 mg/kg on day −1, and 0.2 mg/kg on day 0. The BAL fluids were harvested 1 h after the *Alternaria* extract-challenge on day 0. B, The protein level of IL-33 in the BAL fluid was measured by ELISA. n=4 for PBS-challenged groups, and n=8 for *Alternaria* extract-challenged groups. C, Quantity of DUOX1mRNA expression in the lung was measured by real-time PCR. n=5 for each group. The all results are combined with 2 independent experiments, and shown as mean±S.E.M. Veh=vehicle. PBS=phosphate buffered saline. *P<0.05

GLP-1R Agonist Treatment Suppresses *Alternaria* Extract-Induced IL-33 Release in the BAL Fluid Airborne allergens, such as *Alternaria* have proteolytic activity which induces IL-33 release in bronchoalveolar lavage (BAL) fluid 1 h after airway administration through PAR2 signaling.[26] IL-33 protein levels were measured in BAL fluid 1 h after first *Alternaria* extract-challenge following GLP-1R agonist or vehicle treatment (FIG. 3, A). *Alternaria* extract-challenge significantly increased the protein level of IL-33 in BAL fluid compared with PBS-challenged groups. The *Alternaria* extract-induced IL-33 in BAL fluid was significantly decreased by GLP-1R agonist treatment compared with the vehicle treatment (FIG. 3, B). This result reveals that GLP-1R agonist treatment suppresses acute IL-33 release after *Alternaria* extract-challenge.

GLP-1R Agonist Treatment Suppresses DUOX1 mRNA Expression in the *Alternaria* Extract-Challenged Lung DUOX1 is a critical mediator of IL-33 release from lung epithelial cells following aeroallergen challenge.[5] mRNA expression level of DUOX1 was measured in the lung 1 h after *Alternaria* extract-challenge, the time of peak IL-33 release, following GLP-1R agonist or vehicle treatment. Lung DUOX1 mRNA expression was significantly decreased by GLP-1R agonist treatment compared with vehicle treatment (FIG. 3, C). This result suggests a possible mechanism by which GLP-1R agonist suppressed IL-33 release.

GLP-1R agonist treatment suppresses the number of mouse lung ILC2 expressing IL-5 and IL-13 in response to airway *Alternaria* extract-challenge.

Figure 4:
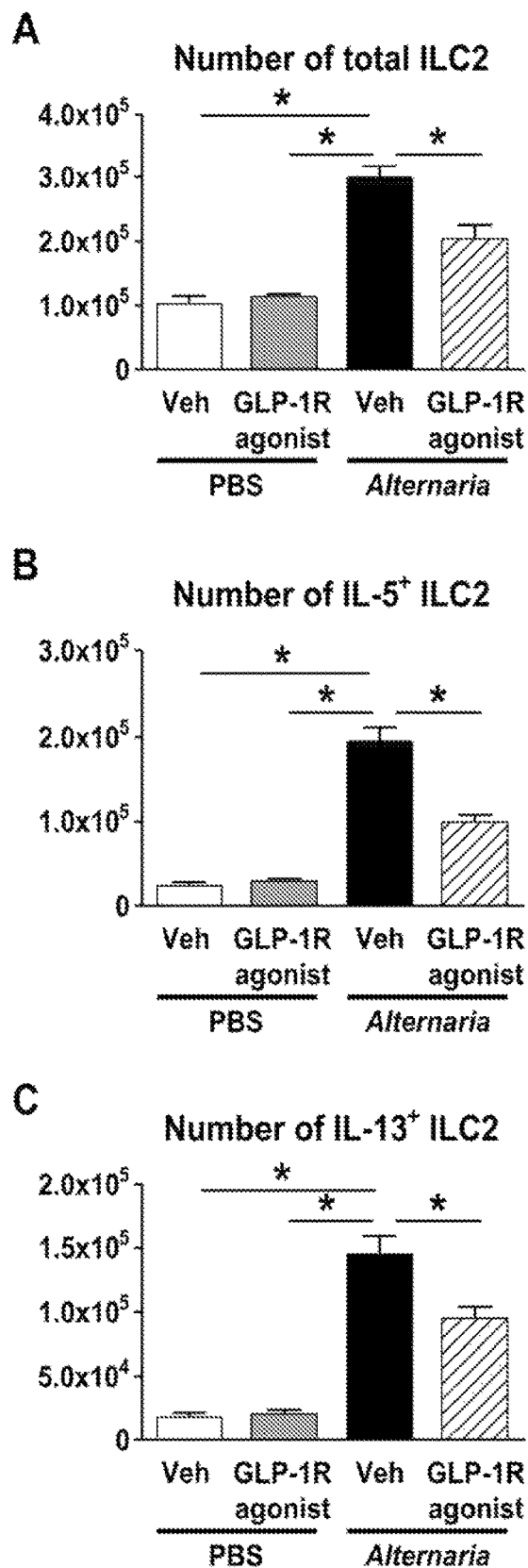
FIG. 4. GLP-1R agonist treatment suppresses the number of mouse lung ILC2 expressing IL-5 and IL-13 in response to airway *Alternaria* extract-challenge. A, Representative histograms of mApple (GLP-1R) expression on ILC2 from WT mice (filled gray area) or GLP-1R/mApple reporter mice (black line). Result is a representative of 3 different mice. B-D, Flow cytometric analysis of the number of total, IL-5+, and IL-13+ ILC2 in the lung. The results are combined with 2 independent experiments, and shown as mean±S.E.M. of 4 mice in PBS-challenged groups and 8 mice in *Alternaria* extract-challenged groups. Veh=vehicle. PBS=phosphate buffered saline. *P<0.05

Since IL-33 is an important stimulus for the innate allergic immune response, it was examined if GLP-1R signaling inhibited ILC2 function. First, GLP-1R expression was measured on lung ILC2 using GLP-1R/mApple reporter mice to reveal whether GLP-1R agonist affect the ILC2 directly. ILC2 were identified as lineage (lin)$^-$CD3$^-$ CD45+CD25+CD127$^+$ cells by cell surface staining. In contrast to epithelial cells and endothelial cells, GLP-1R/mApple expression was not detected on the lung ILC2 (FIG. 4,A). Next, the number of total, IL-5$^+$ and IL-13$^+$ lung ILC2 were enumerated following *Alternaria* extract-challenge for 4 consecutive days to determine the effect of IL-33 reduction by GLP-1R agonist treatment. ILC2 were identified as lineage (lin)$^-$CD3$^-$CD45$^+$CD25$^+$ and ICOS$^+$ instead of CD127, because CD127 expression level was unclear after PMA/ionomycin stimulation (data is not shown). *Alternaria* extract-challenge significantly increased the number of total, IL-5+ and IL-13$^+$ lung ILC2 compared with PBS-challenged mice (FIG. 4, B-C). GLP-1R agonist treatment significantly suppressed the number of *Alternaria* extract-induced total, IL-5+, and IL-13$^+$ lung ILC2 (FIG. 4, B-C) compared with vehicle treatment.

To compare the contribution of CD4 T cells to IL-5 and IL-13 expression, intracellular cytokine staining was performed by flow cytometry. The number of IL-5+ and IL-13+ CD4 T cell were significantly increased in *Alternaria* extract-challenged groups compared to PBS-challenged groups. GLP-1R agonist treatment significantly suppressed the number of *Alternaria* extract-induced CD4 T cells expressing IL-13, but not IL-5. In the *Alternaria* extract-challenged groups, there was a statistically significant 10-fold increase in the number of IL-5$^+$ ILC2 (FIG. 4, B) compared to IL-5$^+$ CD4 T cells (not shown), and a 2.4-fold increase in the number of IL-13$^+$ ILC2 (FIG. 4, C) compared to IL-13$^+$ CD4 T cells (not shown). The fold change between the number of ILC2 and CD4 T cells expressing IL-5 and IL-13 are similar a previous report.[27] Therefore, these results indicate that ILC2, but not CD4 T cells, are the major source of IL-5 and IL-13 in response to this 4 consecutive day airway *Alternaria* extract-challenge protocol, and that GLP-1R signaling inhibits this early innate allergic immune response by the reduction of IL-33 release level in the lung.

GLP-1R agonist treatment suppresses *Alternaria* extract-induced cytokine and chemokine expression in the lung and airway.

Figure 5:
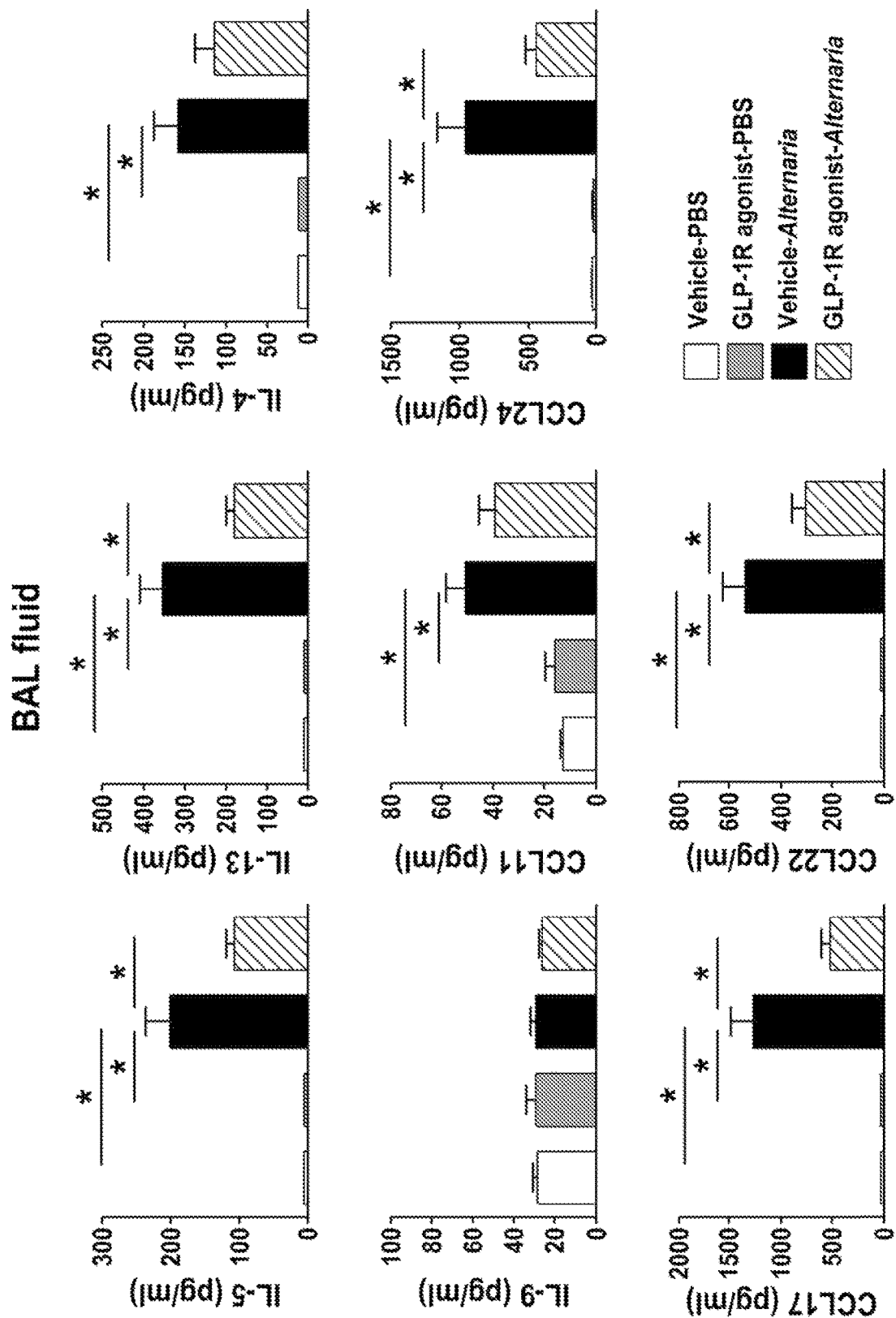
FIG. 5. GLP-1R agonist treatment suppresses *Alternaria* extract-induced cytokine and chemokine expression in the lung and airway. BAL fluid and lungs were harvested 24 h after the last *Alternaria* extract-challenge to measure the protein expression of IL-4, IL-5, IL-9, IL-13, CCL11, CCL17, CCL22, and CCL24 by ELISA. The results are combined with 2 independent experiments, and shown as mean±S.E.M. of 6 mice in PBS-challenged groups and 11 mice in *Alternaria* extract-challenged groups. Veh=vehicle. PBS=phosphate buffered saline. *P<0.05
Figure 5:
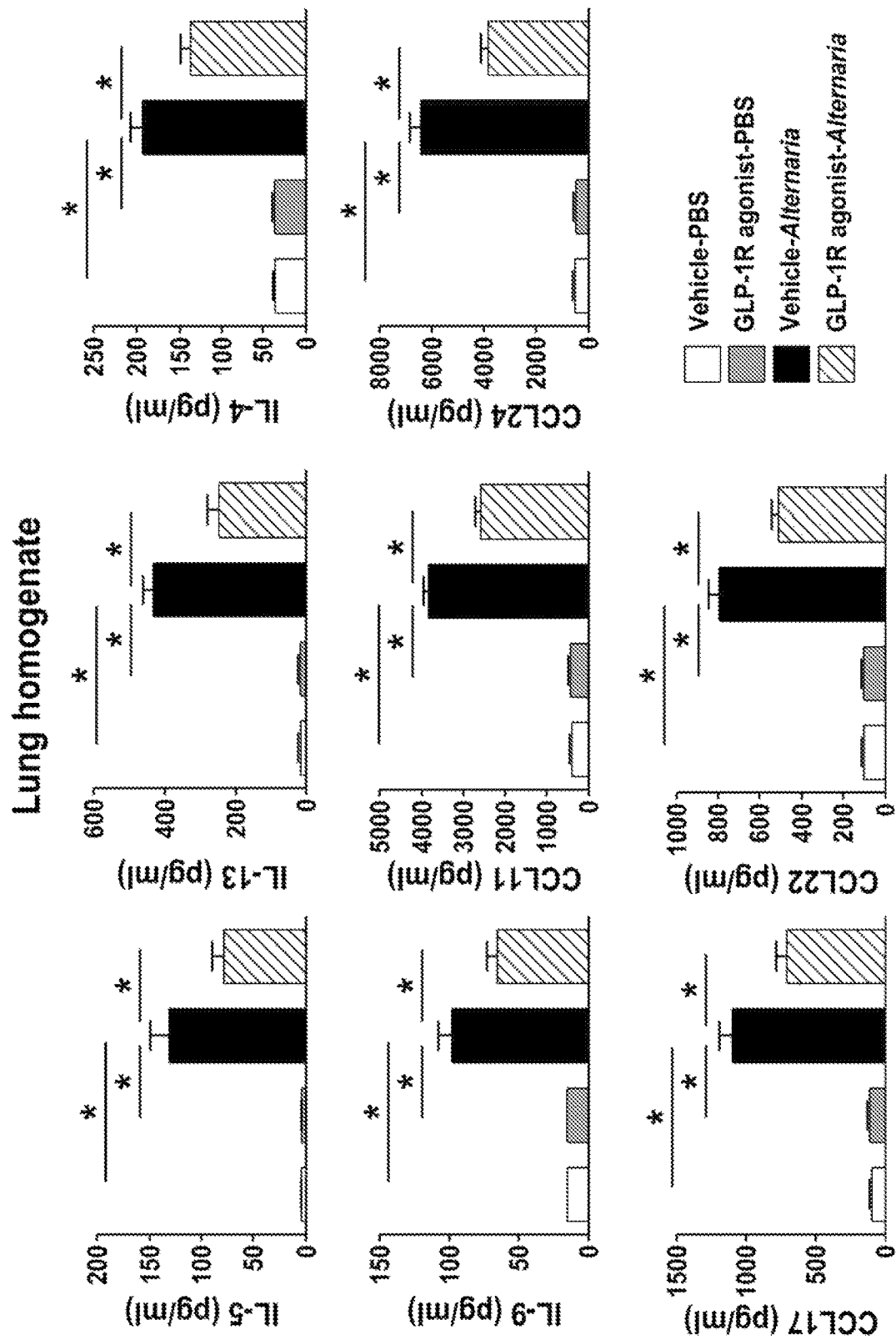

Next, the protein level of type 2 cytokines and chemokines in BAL fluid and lung homogenate were measured. *Alternaria* extract-challenge significantly increased the protein expression of IL-4, IL-5, IL-13, CCL11 (eotaxin), CCL17 (TARC), CCL22 (MDC), and CCL24 (eotaxin-2) in both the BAL fluid and lung homogenates compared with PBS-challenged groups. IL-9 was significantly increased in the lung homogenate, but not BAL fluid following *Alternaria* extract-challenge. A statistically significant decrease was observed in *Alternaria* extract-induced protein expression of IL-5, IL-13, CCL17, CCL 22 and CCL24 in both the BAL fluids and lung homogenates from GLP-1R agonist-treated mice compared with vehicle-treated mice (FIG. 5). In addition, *Alternaria* extract-induced IL-4, IL-9, and CCL11 protein expression was also decreased in the lung homogenates from GLP-1R agonist-treated mice compared with vehicle-treated mice.

GLP-1R agonist treatment suppresses eosinophilia, mucus production, and airway responsiveness in response to airway *Alternaria* extract-challenge.

Figure 6:
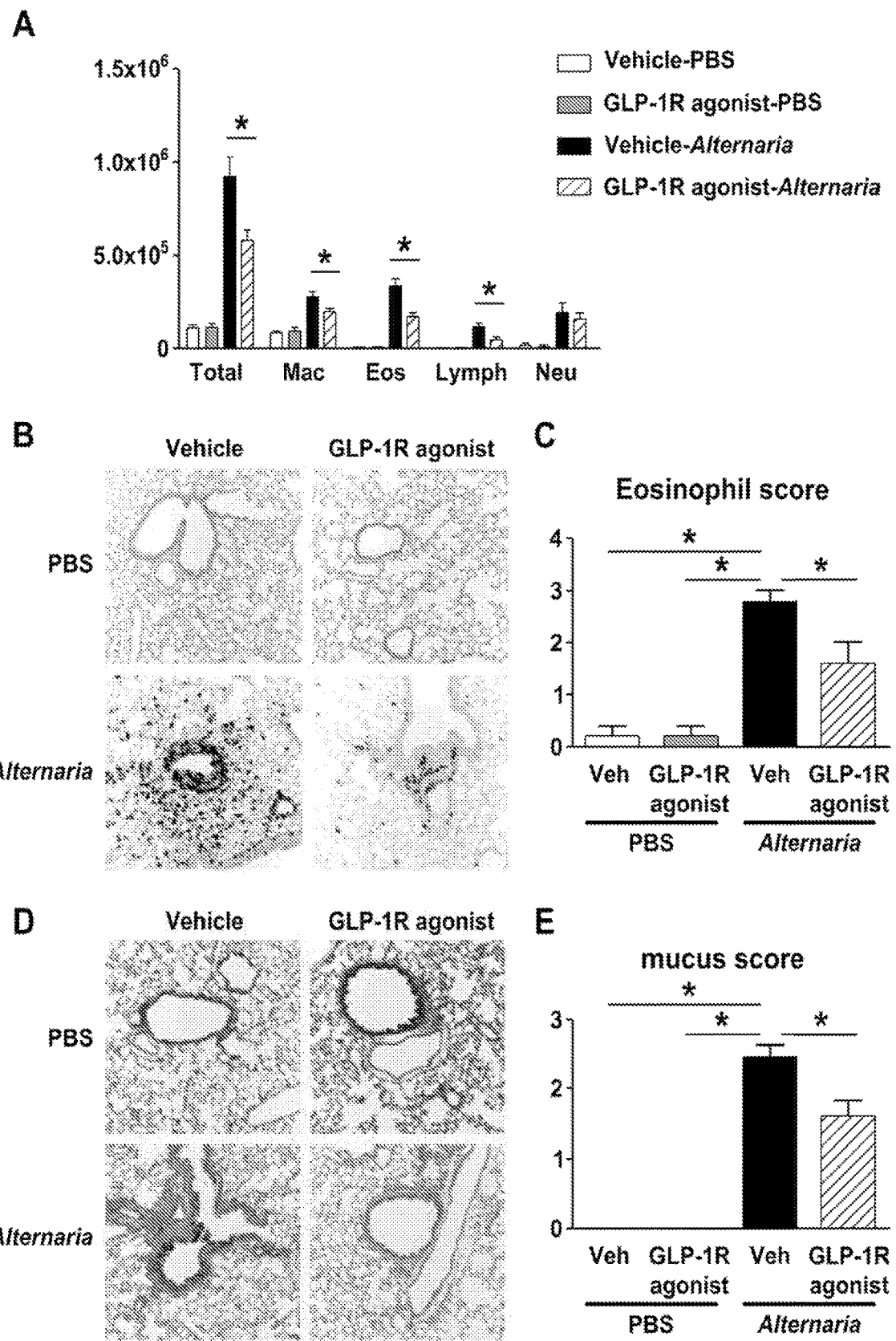
FIG. 6. GLP-1R agonist treatment suppresses eosinophilia, mucus production, and airway responsiveness in response to airway *Alternaria* extract-challenge. A, Cell differentials from BAL fluid harvested 24 h after the last *Alternaria* extract-challenge. n=6 for PBS-challenged groups, and n=11 for *Alternaria* extract-challenged groups. B, Representative sections and C, eosinophil score as determined by anti-MBP antibody staining. n=5 for each group. D, Representative sections and E, mucus score as determined by PAS staining. n=4 for PBS-challenged groups, and n=10 for *Alternaria* extract-challenged groups. The lungs for histological analysis were harvested 48 h after the last *Alternaria* extract-challenge. F, Airway resistance to increasing dose of methacholine challenge. n=7 for PBS-challenged groups, and n=16 for *Alternaria* extract-challenged groups (*P<0.05 compared with vehicle-PBS. **P<0.05 compared with vehicle-*Alternaria*). The all results are combined with 2 independent experiments, and shown as mean±S.E.M. Veh=vehicle. PBS=phosphate buffered saline. Mch=methacholine. *P<0.05
Figure 6:
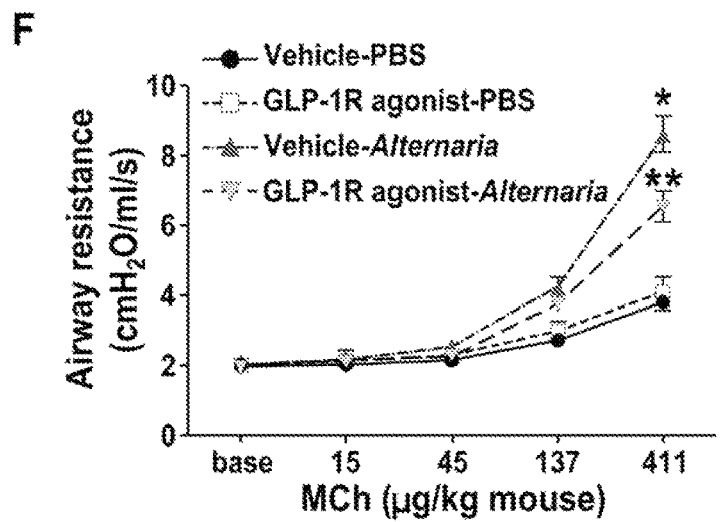

Based on the finding that GLP-1R agonist treatment significantly decreased protein expression of *Alternaria* extract-induced IL-5, CCL11, and CCL24 that are associated with eosinophil recruitment, GLP-1R agonist treatment was investigated to see if it decreases eosinophil accumulation in the lung following *Alternaria* extract-challenge. BAL cell counts and differentials were measured, and assessed perivascular eosinophils by immunohistopathology. *Alternaria* extract-challenge significantly increased the number of total BAL cells, macrophages, eosinophils, lymphocytes and neutrophils compared with PBS-challenged groups. GLP-1R agonist treatment significantly decreased the number of *Alternaria* extract-induced total BAL cells, macrophages, eosinophils, and lymphocytes compared with vehicle treatment (FIG. 6, A). Further, GLP-1R agonist treatment resulted in a significant decrease of *Alternaria* extract-induced perivascular eosinophils in the lung compared with vehicle treatment by immunohistopathology (FIGS. 6, B and C).

IL-13 is a critical inducer of airway mucus production.[28] It was found that GLP-1R agonist treatment decreased protein level of IL-13 in the lung. Therefore, GLP-1R agonist treatment was tested to see if it suppresses mucus production in the airway following *Alternaria* extract-challenge. There was no mucus or mucous producing cells in the lungs of mice challenged with PBS. *Alternaria* extract-challenge significantly increased mucus production on large airway epithelial cells. GLP-1R agonist treatment significantly decreased the *Alternaria* extract-induced mucus production compared with vehicle treatment (FIGS. 6, D and E). These results indicate that GLP-1R agonist treatment suppresses acute eosinophilic lung inflammation and airway mucus production in innate allergic immune responses to *Alternaria* extract-challenge.

It was found that GLP-1R agonist treatment significantly decreased asthma-like airway inflammation following *Alternaria* extract-challenge for 4 consecutive days. Next, GLP-1R agonist treatment was tested to see if it would decrease airway responsiveness (AR) in *Alternaria* extract-challenged mice. *Alternaria* extract-challenge significantly increased AR compared with PBS challenge. GLP-1R agonist treatment significantly decreased the *Alternaria* extract-induced AR compared with vehicle treatment (FIG. 6, F).

Discussion

These results show that a GLP-1R agonist inhibited lung epithelial expression and airway release of IL-33 in response to the clinically relevant, protease-containing, ubiquitous aeroallergen, *Alternaria alternata*. This is the first report of an FDA approved pharmacologic agent inhibiting allergen-induced lung IL-33 expression and release. These findings provide methods for use of GLP-1R agonists as an alternative to biologic therapies such as monoclonal antibodies or receptor antagonists that target IL-33-mediated diseases. In addition, DUOX1 mRNA was also decreased by GLP-1R agonist treatment during IL-33 release following *Alternaria* extract-challenge. Further, it was found that GLP-1R agonist treatment significantly decreased the number of lung ILC2 expressing IL-5 and IL-13 following 4 consecutive days of *Alternaria* extract-challenge. GLP-1R agonist treatment significantly decreased IL-4, IL-5, IL-9, IL-13, CCL11, CCL17, CCL22 and CCL24 protein expression in the lung homogenates, the number of eosinophils in the BAL fluid and perivascular eosinophil accumulation, mucus production, and AR induced by the *Alternaria* extract-challenge. These results show that GLP-1R signaling not only has an effect on allergen-induced IL-33 release in the airway, but also has downstream inhibitory effects on the cells that produce Type 2 cytokines that drive allergic inflammation.

GLP-1R is abundantly expressed in human and mouse lung, heart, brain and kidney as well as pancreas,[29,30] and many studies indicate the therapeutic effect of GLP-1R signaling for diseases in multiple tissues. For instance, a GLP-1R agonist, exendin-4, improved atherosclerosis by reducing macrophage adhesion to endothelial cells as well as by reducing serum glucose level.[30] GLP-1 peptide treatment decreased irradiation- or LPS-induced proinflammatory cytokine expression in the brain and astrocytes in a mouse model.[31, 32] In addition, GLP-1R agonist decreased chronic lung inflammation in a mouse model of OVA sensitization combined with 66 days of OVA challenge,[20] and reduced mortality and airway resistance in a mouse model of obstructive lung disease induced by OVA and LPS challenge.[33]

Binding of GLP-1 to its G protein coupled receptor causes adenylate cyclase activation resulting in the formation of cyclic adenosine monophosphate (cAMP). Subsequent activation of protein kinase A (PKA) and the cAMP-regulated guanine nucleotide exchange factor II (cAMP-GEFII) leads to an elevation of intracellular calcium concentrations, and enhanced exocytosis of insulin-containing granules in pancreatic β-cells.[34] Further, β2 adrenergic receptor signaling also activate the cAMP/PKA signaling pathway, and then relaxed airway smooth muscle and reduced airway mucus secretion.[35] Prostaglandin I2 (PGI2) receptor signaling down-regulated DC, T cell, and ILC2 activation mediated by cAMP induction.[36-38]

In addition, GLP-1R agonist reduced inflammatory responses in mouse peritoneal macrophages stimulated with LPS through cAMP signaling pathway.[35] These results show that cAMP induction by GLP-1R agonist as well as β2 adrenergic agonist or PGI2 may have suppressive effects on the activation of immune cells that express GLP-1R.

In this study, GLP-1R agonist treatment down-regulated *Alternaria* extract-induced IL-33 release and expression. IL-33 plays important roles in type-2 innate immunity following helminth infection or after exposure to protease containing aeroallergens.[25, 40] Biologically active full length IL-33 is released into the extracellular space after cell damage such as necrosis, and then IL-33 activates many types of immune cells, including CD4 T cells, mast cells, basophils, macrophages, DCs, and epithelial cells as well as ILC2.[41, 42] IL-33 is likely to be a first alarm signal due to its constitutive expression in normal epithelial and endothelial cells,[42] and is ready to be released following infection or mechanical cell damage. GLP-1R agonist treatment reduced IL-33 release and DUOX1 mRNA expression after the first *Alternaria* extract challenge. Hristova and colleagues reported that *Alternaria* induced IL-33 release in cultured primary human bronchial epithelial cells (HBE) depended critically on DUOX1-mediated activation.[26] Shiraki and colleagues reported that GLP-1R signaling inhibited NADPH oxidase activation in primary human endothelial cells.[43] Taken together, these findings show that GLP-1R signaling decreases DUOX1 expression in the lung epithelial cells, thus inhibiting *Alternaria*-induced IL-33 secretion.

The reduction in IL-33 protein level to airway *Alternaria* extract-challenge mediated by the GLP-1R agonist is one possible mechanism by which GLP-1R signaling reduced the number of IL-5 and IL-13 expressing ILC2 and protein levels of CCL11, CCL24, TARC, and MDC in the airway and lung following 4 consecutive days *Alternaria* extract-challenge. These findings are consistent with previous reports that IL-33 induced IL-5 and IL-13 expression by ILC2 in dose-dependent fashion,[44] CCL11 expression by fibroblast,[45] and TARC expression by DCs.[46]

While it was found that GLP-1R was not expressed on lung ILC2, previous studies reported that GLP-1R was expressed in mouse peritoneal macrophage, human monocyte cell line THP-1,[39] and human invariant natural killer T (iNKT) cell line.[47]

In the 4 consecutive days of *Alternaria* extract-challenge model, the number of IL-5 and IL-13 expressing CD4 T cells was statistically significantly less than the number of IL-5 and IL-13 expressing ILC2, and a previous report showed that total IgE and antigen specific IgG1 in serum were no different between naïve mice and mice challenged with *Alternaria* extract for 4 consecutive days.[38] This supports the concept that the innate immune system, and not adaptive immunity, initiate and promotes type 2 allergic airway inflammation in this mouse model of allergen challenge. Taken together, these findings reveal that GLP-1R signaling suppresses aeroallergen-driven IL-33 release and inhibits ILC2-dependent innate type 2 airway inflammation. Currently, biological agents are in development to antagonize IL-33 for the treatment of atopic dermatitis, food allergy, and asthma.[9] These results show that a currently FDA approved GLP-1R antagonist inhibits allergen-induced IL-33 release and expression.

In summary, it was found that GLP-1R agonist treatment down-regulated IL-33 release and expression, and innate allergic airway inflammation, including lung eosinophilia, mucus hypersecretion and AR following 4 consecutive days of *Alternaria* extract-challenge. These results show that GLP-1R agonists constitute a novel therapeutic approach for allergic asthma induced by protease-containing aeroallergens.

REFERENCES CITED IN THIS EXAMPLE

1. Li X, Ampleford E J, Howard T D, Moore W C, Torgerson D G, Li H, et al. Genome-wide association studies of asthma indicate opposite immunopathogenesis direction from autoimmune diseases. J Allergy Clin Immunol 2012; 130: 861-868
2. Nieuwenhuis M A, Siedlinski M, van den Berge M, Granell R, Li X, Niens M, et al. Combining genomewide association study and lung eQTL analysis provides evidence for novel genes associated with asthma. Allergy 2016; August 22.
3. Ober C, Yao T-C. The genetics of asthma and allergic disease: a 21st century perspective. Immunological Reviews 2011; 242:10-30.
4. Savenije O E, Mahachie John J M, Granell R, Kerkhof M, Dijk F N, de Jongste J C, et al. Association of IL33-IL-1 receptor-like 1 (IL1RL1) pathway polymorphisms with wheezing phenotypes and asthma in childhood. J Allergy Clin Immunol 2014; 134: 170-177.
5. Hristova M, Habibovic A, Veith C, Janssen-Heininger Y M, Dixon A E, Geiszt M, et al. Airway epithelial dual oxidase 1 mediates allergen-induced IL-33 secretion and activation of type 2 immune responses. J Allergy Clin Immunol 2015; 137:1545-1556
6. Halim Timotheus Y F, Krauß Ramona H, Sun Ann C, Takei F. Lung Natural Helper Cells Are a Critical Source of Th2 Cell-Type Cytokines in Protease Allergen-Induced Airway Inflammation. Immunity 2012; 36: 451-463.
7. Bartemes K R, Iijima K, Kobayashi T, Kephart G M, McKenzie A N, Kita H. IL-33-responsive lineage-CD25+CD44(hi) lymphoid cells mediate innate type 2 immunity and allergic inflammation in the lungs. J Immunol 2012; 188: 1503-1513.
8. Kurowska-Stolarska M, Kewin P, Murphy G, Russo R C, Stolarski B, Garcia C C, et al. IL-33 induces antigen-specific IL-5+ T cells and promotes allergic-induced airway inflammation independent of IL-4. J Immunol 2008; 181: 4780-90.
9. Borish L. The immunobiology of asthma: Asthma phenotypes and their implications for personalized treatment. Ann Allergy Asthma Immunol 2016; 117:108-114.
10. Lim G E, Brubaker P L. Glucagon-Like Peptide 1 Secretion by the L-Cell: The View From Within. Diabetes 2006; 55: S70-S77.
11. Vilsboll T, Toft-Nielsen M B, Krarup T, Madsbad S, Dinesen B, Holst J J. Evaluation of beta-cell secretory capacity using glucagon-like peptide 1. Diabetes Care 2000; 23: 807-812.
12. De Marinis Y Z, Salehi A, Ward C E, Zhang Q, Abdulkader F, Bengtsson M, et al. GLP-1 inhibits and adrenaline stimulates glucagon release by differential modulation of N- and L-type Ca2+ channel-dependent exocytosis. Cell Metab 2010; 11: 543-553.
13. Spreckley E, Murphy K G. The L-Cell in Nutritional Sensing and the Regulation of Appetite. Front Nutr 2015; 2: 23.
14. Egan A G, Blind E, Dunder K, de Graeff P A, Hummer B T, Bourcier T, et al. Pancreatic safety of incretin-based drugs-FDA and EMA assessment. N Engl J Med 2014; 370: 794-797.
15. Divino V, DeKoven M, Hallinan S, Varol N, Wirta S B, Lee W C, et al. Glucagon-like Peptide-1 receptor agonist treatment patterns among type 2 diabetes patients in six European countries. Diabetes Ther 2014; 5: 499-520.
16. Hogan A E, Gaoatswe G, Lynch L, Corrigan M A, Woods C, O'Connell J, et al. Glucagon-like peptide 1 analogue therapy directly modulates innate immune-mediated inflammation in individuals with type 2 diabetes mellitus. Diabetologia 2014; 57: 781-784.
17. Lee Y S, Park M S, Choung J S, Kim S S, Oh H H, Choi C S, et al. Glucagon-like peptide-1 inhibits adipose tissue macrophage infiltration and inflammation in an obese mouse model of diabetes. Diabetologia 2012; 55: 2456-2468.
18. Yanay O, Bailey A L, Kernan K, Zimmerman J J, Osborne W R. Effects of exendin-4, a glucagon like peptide-1 receptor agonist, on neutrophil count and inflammatory cytokines in a rat model of endotoxemia. J Inflamm Res 2015; 8: 129-135.
19. Wang Y, Parlevliet E T, Geerling J J, van der Tuin S J, Zhang H, Bieghs V, et al. Exendin-4 decreases liver inflammation and atherosclerosis development simultaneously by reducing macrophage infiltration. Br J Pharmacol 2014; 171: 723-734.
20. Gou S, Zhu T, Wang W, Xiao M, Wang X C, Chen Z H. Glucagon like peptide-1 attenuates bleomycin-induced pulmonary fibrosis, involving the inactivation of NF-kappaB in mice. Int Immunopharmacol 2014; 22: 498-504.
21. Zhu T, Wu X L, Zhang W, Xiao M. Glucagon Like Peptide-1 (GLP-1) Modulates OVA-Induced Airway Inflammation and Mucus Secretion Involving a Protein Kinase A (PKA)-Dependent Nuclear Factor-kappaB (NF-kappaB) Signaling Pathway in Mice. Int J Mol Sci 2015; 16: 20195-20211.
22. Kouzaki H, Iijima K, Kobayashi T, O'Grady S M, Kita H. The danger signal, extracellular ATP, is a sensor for an airborne allergen and triggers IL-33 release and innate Th2-type responses. J Immunol 2011; 186:4375-4387.
23. O'Hollaren M T, Yunginger J W, Offord K P, Somers M J, O'Connell E J, Ballard D J, et al. Exposure to an aeroallergen as a possible precipitating factor in respiratory arrest in young patients with asthma. N Engl J Med 1991; 324:359-63.
24. Hardman C S, Panova V, McKenzie A N J. IL-33 citrine reporter mice reveal the temporal and spatial expression of IL-33 during allergic lung inflammation. European Journal of Immunology 2013; 43: 488-498.
25. Reddy I A, Pino J A, Weikop P, Osses N, Sorensen G, Bering T, et al. Glucagon-like peptide 1 receptor activation regulates cocaine actions and dopamine homeostasis in the lateral septum by decreasing arachidonic acid levels. Transl Psychiatry 2016; 6: e809.
26. Snelgrove R J, Gregory L G, Peiró T, Akthar S, Campbell G A, Walker S A, et al. *Alternaria*-derived serine protease activity drives IL-33-mediated asthma exacerbations. Journal of Allergy and Clinical Immunology 2014; 134: 583-592.e586.
27. Toki S, Goleniewska K, Reiss S, Zhou W, Newcomb D C, Bloodworth M H, et al. The histone deacetylase inhibitor trichostatin A suppresses murine innate allergic inflammation by blocking group 2 innate lymphoid cell (ILC2) activation. Thorax 2016; 71: 633-645.

28. Zhu Z, Homer R J, Wang Z, Chen Q, Geba G P, Wang J, et al. Pulmonary expression of interleukin-13 causes inflammation, mucus hypersecretion, subepithelial fibrosis, physiologic abnormalities, and eotaxin production. J Clin Invest 1999; 103: 779-788.
29. Pyke C, Heller R S, Kirk R K, Ørskov C, Reedtz-Runge S, Kaastrup P, et al. GLP-1 Receptor Localization in Monkey and Human Tissue: Novel Distribution Revealed With Extensively Validated Monoclonal Antibody. Endocrinology 2014; 155: 1280-1290.
30. Arakawa M, Mita T, Azuma K, Ebato C, Goto H, Nomiyama T, et al. Inhibition of Monocyte Adhesion to Endothelial Cells and Attenuation of Atherosclerotic Lesion by a Glucagon-like Peptide-1 Receptor Agonist, Exendin-4. Diabetes 2010; 59: 1030-1037.
31. Parthsarathy V, Holscher C. The type 2 diabetes drug liraglutide reduces chronic inflammation induced by irradiation in the mouse brain. European Journal of Pharmacology 2013; 700: 42-50.
32. Iwai T, Ito S, Tanimitsu K, Udagawa S, Oka J-I. Glucagon-like peptide-1 inhibits LPS-induced IL-1β production in cultured rat astrocytes. Neuroscience Research 2006; 55: 352-360.
33. Viby N-E, Isidor M S, Buggeskov K B, Poulsen S S, Hansen J B, Kissow H. Glucagon-Like Peptide-1 (GLP-1) Reduces Mortality and Improves Lung Function in a Model of Experimental Obstructive Lung Disease in Female Mice. Endocrinology 2013; 154: 4503-4511.
34. Hoist J J. The physiology of glucagon-like peptide 1. Physiol Rev 2007; 87: 1409-1439.
35. Billington C K, Ojo O O, Penn R B, Ito S. cAMP regulation of airway smooth muscle function. Pulmonary Pharmacology & Therapeutics 2013; 26: 112-120.
36. Zhou W, Blackwell T S, Goleniewska K, O'Neal J F, Fitzgerald G A, Lucitt M, et al. Prostaglandin I$_2$ analogs inhibit Th1 and Th2 effector cytokine production by CD4 T cells. J Leukoc Biol 2007; 81: 809-817.
37. Zhou W, Hashimoto K, Goleniewska K, O'Neal J F, Ji S, Blackwell T S, et al. Prostaglandin I$_2$ analogs inhibit proinflammatory cytokine production and T cell stimulatory function of dendritic cells. J Immunol 2007; 178: 702-710.
38. Zhou W, Toki S, Zhang J, Goleniewksa K, Newcomb D C, Cephus J Y, et al. Prostaglandin 12 Signaling and Inhibition of Group 2 Innate Lymphoid Cell Responses. Am J Respir Crit Care Med 2016; 193: 31-42.
39. Arakawa M, Mita T, Azuma K, Ebato C, Goto H, Nomiyama T, et al. Inhibition of Monocyte Adhesion to Endothelial Cells and Attenuation of Atherosclerotic Lesion by a Glucagon-like Peptide-1 Receptor Agonist, Exendin-4. Diabetes 2010; 59:1030-1037.
40. Hung L Y, Lewkowich I P, Dawson L A, Downey J, Yang Y, Smith D E, et al. IL-33 drives biphasic IL-13 production for noncanonical Type 2 immunity against hookworms. Proc Natl Acad Sci USA 2013; 110: 282-287.
41. Kurowska-Stolarska M, Hueber A, Stolarski B, McInnes I B. Interleukin-33: a novel mediator with a role in distinct disease pathologies. Journal of Internal Medicine 2011; 269: 29-35.
42. Cayrol C, Girard J-P. IL-33: an alarmin cytokine with crucial roles in innate immunity, inflammation and allergy. Current Opinion in Immunology 2014; 31: 31-37.
43. Shiraki A, Oyama J, Komoda H, Asaka M, Komatsu A, Sakuma M, Kodama K et al. The glucagon-like peptide 1 analog liraglutide reduces TNF-alpha-induced oxidative stress and inflammation in endothelial cells. Atherosclerosis 2012; 221:375-382.
44. Mohapatra A, Dyken S J V, Schneider C, Nussbaum J C, Liang H-E, Locksley R M. Group 2 innate lymphoid cells utilize the IRF4-IL-9 module to coordinate epithelial cell maintenance of lung homeostasis. Mucosal Immunol 2016; 1:275-286
45. Kurokawa M, Matsukura S, Kawaguchi M, leki K, Suzuki S, Odaka M, et al. Expression and Effects of IL-33 and ST2 in Allergic Bronchial Asthma: IL-33 Induces Eotaxin Production in Lung Fibroblasts. International Archives of Allergy and Immunology 2011; 155: 12-20.
46. Besnard A-G, Togbe D, Guillou N, Erard F, Quesniaux V, Ryffel B. IL-33-activated dendritic cells are critical for allergic airway inflammation. European Journal of Immunology 2011; 41: 1675-1686.
47. Hogan A E, Tobin A M, Ahern T, Corrigan M A, Gaoatswe G, Jackson R. et al. Glucagon-like peptide-1 (GLP-1) and the regulation of human invariant natural killer T cells: lessons from obesity, diabetes and psoriasis. Diabetologia 2011; 54:2745-2754

Example 2. Glucagon-Like Peptide-1 Receptor Signaling Attenuates RSV-Induced Type 2 Responses and Immunopathology Glucagon-like peptide-1 receptor (GLP-1R) agonists, which potentiate insulin and suppress glucagon secretion, are a well-accepted and safe treatment for Type II diabetes.[1] Although GLP-1R agonists are currently used for their ability to potentiate insulin and suppress glucagon secretion, recent evidence suggests that GLP-1R signaling also has anti-inflammatory effects.[2-4] Severe RSV-associated illness is in part caused by IL-13 production, which mediates the mucus production that directly contributes to airway obstruction and respiratory failure.[5] In this example, it was investigated whether GLP-1R signaling inhibits IL-13-mediated immunopathology of RSV 12/12-6, a strain of RSV that was isolated from a hospitalized infant with severe lower respiratory tract infection and bronchiolitis.

Figure 7:
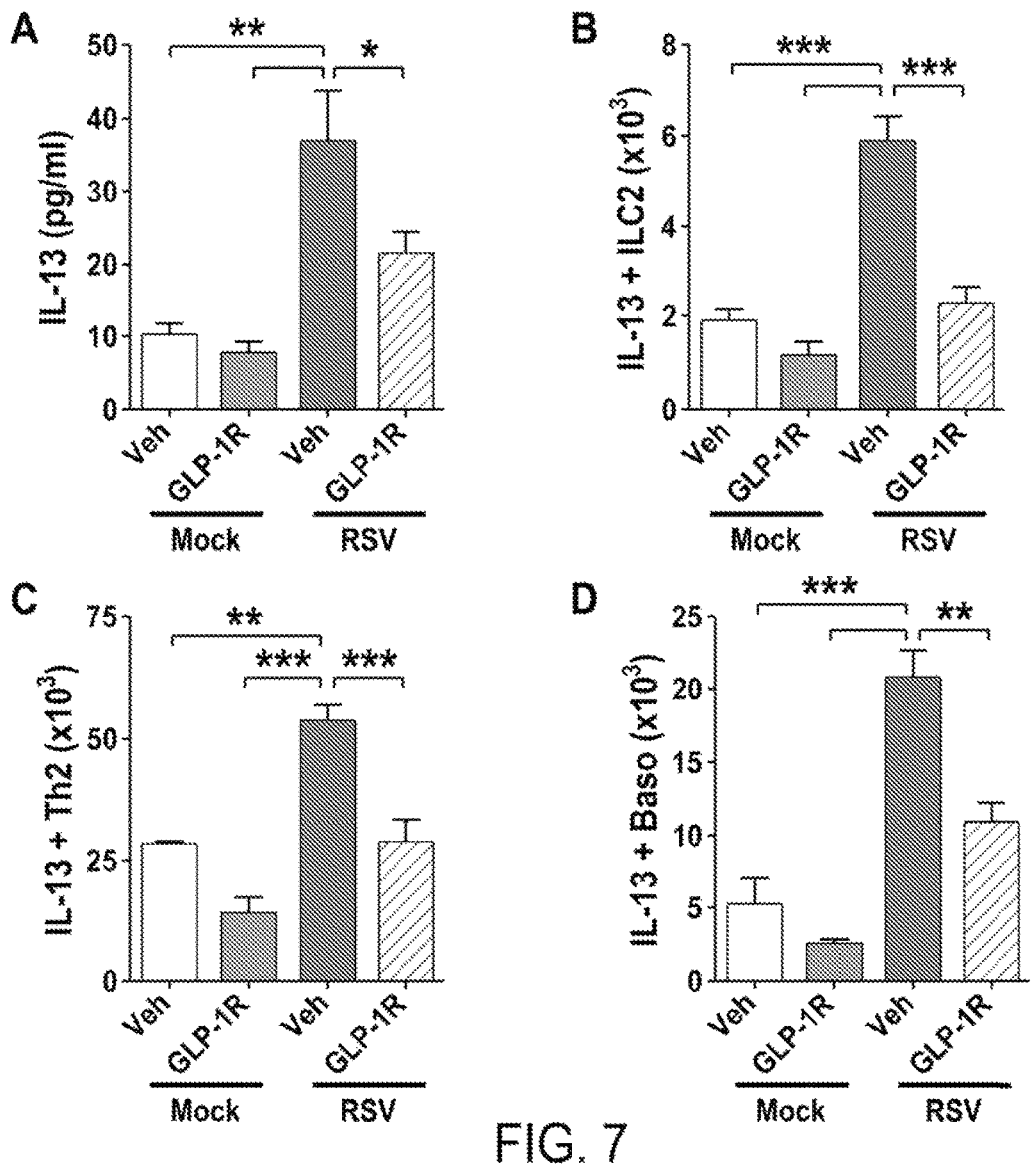
FIG. 7. GLP-1R agonist decreases RSV-induced type 2 responses and immunopathology. (A) ELISA for IL-13 in whole lung homogenate (right lung only). (B) Total number of IL-13$^+$ ILC2, (C) Th2 cells, and (D) basophils. (E) Representative IL-13 expression measured by flow cytometry in ILC2. (F) Representative PAS-stained section of mucus-containing airways in the lungs (40× magnification); arrowhead denotes intraluminal mucus strand. (G) Quantification of airway mucus from the experiment in A. (H) Airway responsiveness and (I) BAL cell counts. Data plotted as mean+SEM. n=3-6 mice per group representative of 3 (A) or 2 (B-G & I) independent experiments. n=6-12 mice per group combined from 2 independent experiments (H). *p<0.05, p<0.01, *p<0.001 by one-way (B & E-H) or two-way (C-D) ANOVA. BL=baseline.
Figure 7:
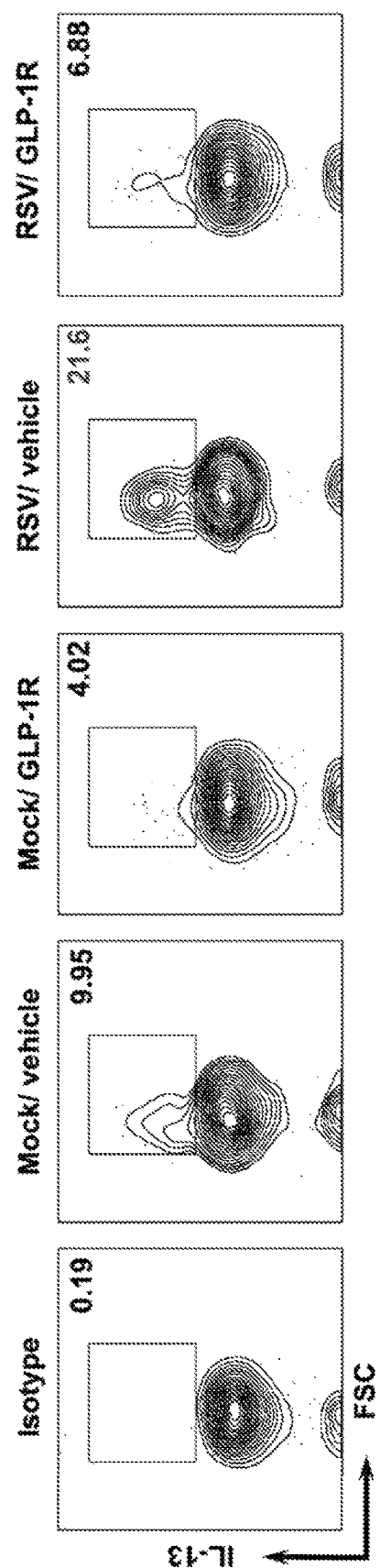
Figure 7:
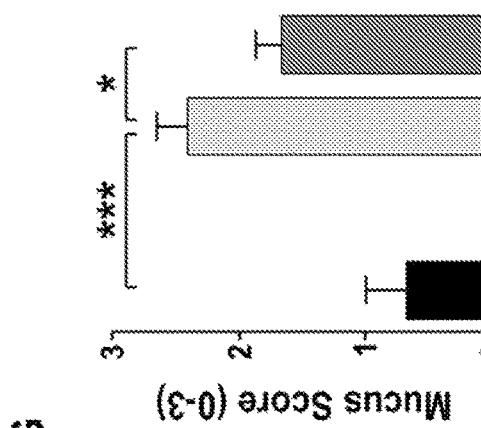
Figure 7:
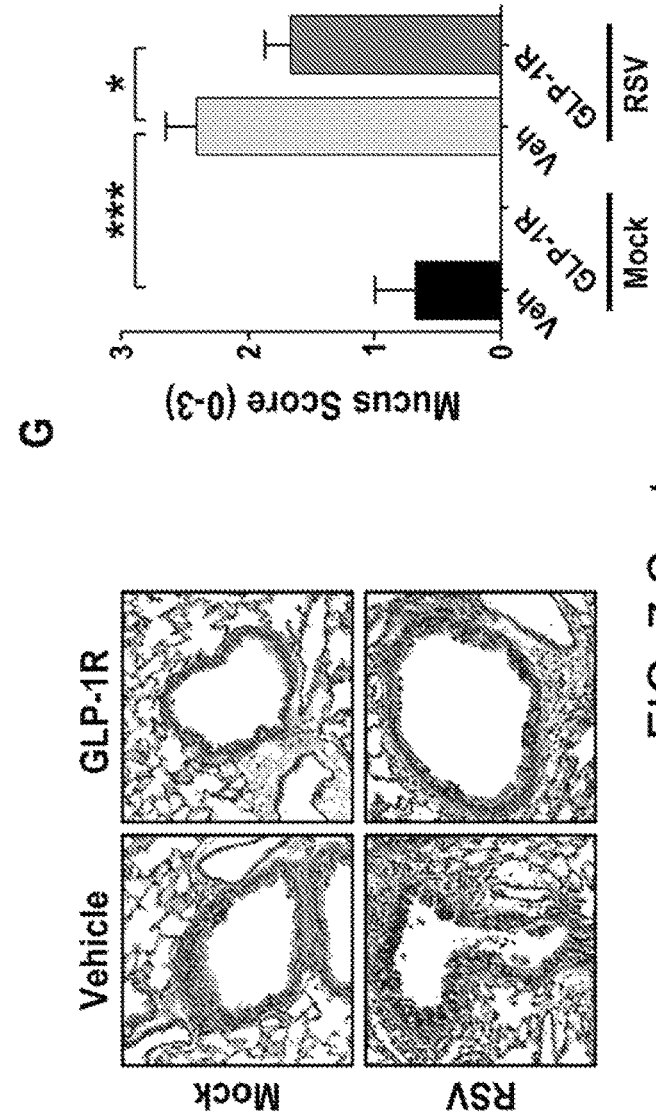
Figure 7:
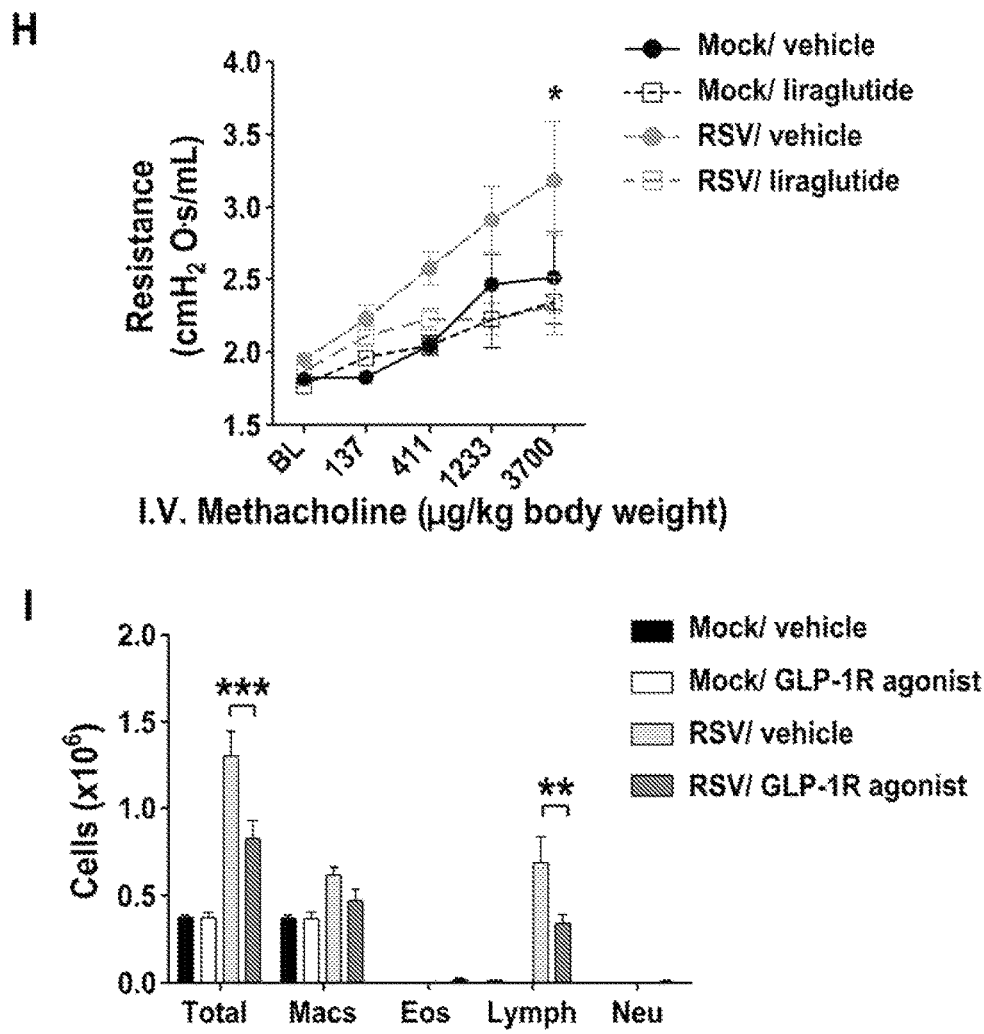

Eight-week old mice were infected with $9 \times 10^5$ PFU of RSV. RSV 12/12-6 induced significant lung IL-13 and airway mucus, mimicking what is seen in patients with severe infection (FIG. 9). GLP-1R agonist or vehicle (0.1% BSA in PBS) were administered twice daily beginning 2 days prior to RSV infection until all endpoints (FIG. 10). GLP-1R agonist treatment significantly decreased lung IL-13 protein expression compared to vehicle treatment in RSV-infected mice (FIG. 7, A). The cellular sources of IL-13 that GLP-1R signaling was inhibiting were identified. GLP-1R agonist treatment in RSV-infected mice significantly decreased the total number of cells in the lung, the total number of group 2 innate lymphoid cells (ILC2), and the percentage of ILC that were IL-13+ compared to RSV-infected vehicle-treated mice (FIG. 11A, FIGS. 12A&F & FIGS. 7, B&E). There was significantly decreased MFI of IL-13 and CD127 on the ILC2 of RSV-infected GLP-1R agonist-treated mice compared to RSV-infected vehicle-treated mice, indicating decreased IL-13 production and CD127 expression on a per ILC2 basis with GLP-1R agonist treatment (FIG. 12B-E). GLP-1R agonist treatment in RSV-infected mice significantly decreased the numbers of CD4+ T cells and basophils, as well as IL-13+ Th2 cells and basophils compared to RSV-infected vehicle-treated mice (FIG. 11B-C, FIG. 12G-H & FIG. 7, C-D).

Moreover, there were significant decreases in methacholine-induced airway responsiveness and mucus severity scores in RSV-infected GLP-1R agonist-treated mice compared to RSV-infected vehicle-treated mice (FIG. 7, F-H).

RSV-infected GLP-1R agonist-treated mice had significantly decreased numbers of total bronchoalveolar lavage (BAL) cells and lymphocytes compared to RSV-infected vehicle-treated mice (FIG. 7, I). Administration of the GLP-1R agonist beginning 2 days after RSV infection also significantly decreased lung IL-13 and there was a trend towards decreased airway mucus (FIG. 13). Collectively, these data demonstrate that GLP-1R signaling attenuates IL-13-mediated immunopathology during RSV infection.

Figure 8:
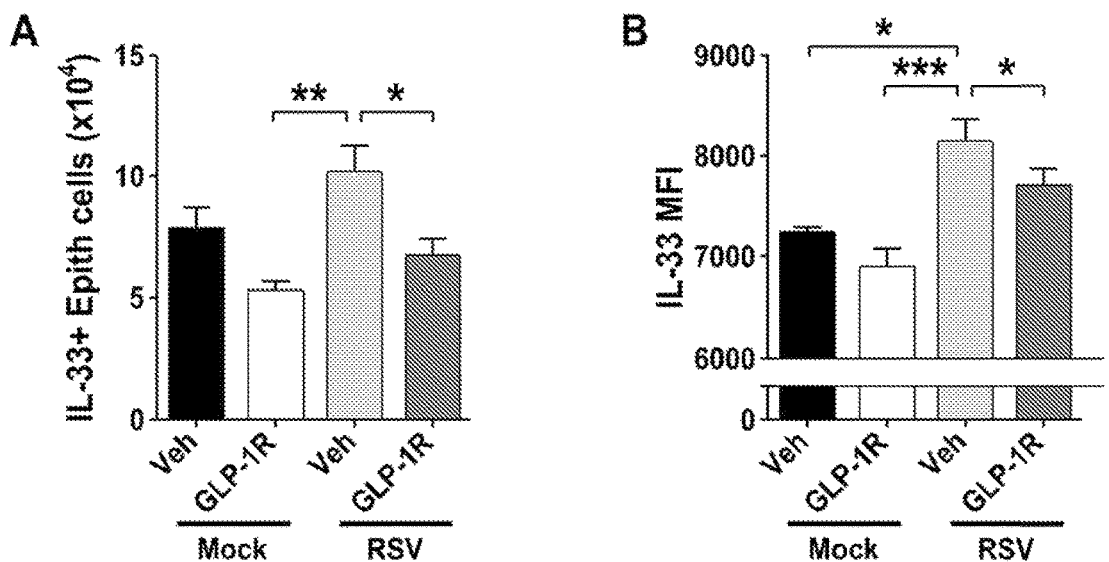
FIG. 8. GLP-1R signaling decreases IL-33, does not increase viral titer or decrease IFN-γ production, and associates with acute bronchiolitis in humans. (A) Total number of IL-33$^+$ epithelial cells, (B) MFI of IL-33 expression in epithelial cells, (C) representative IL-33 expression measured by flow cytometry in epithelial cells, and (D) ELISA for IL-33 in whole lung homogenate (left lung only). (E)
Figure 8:
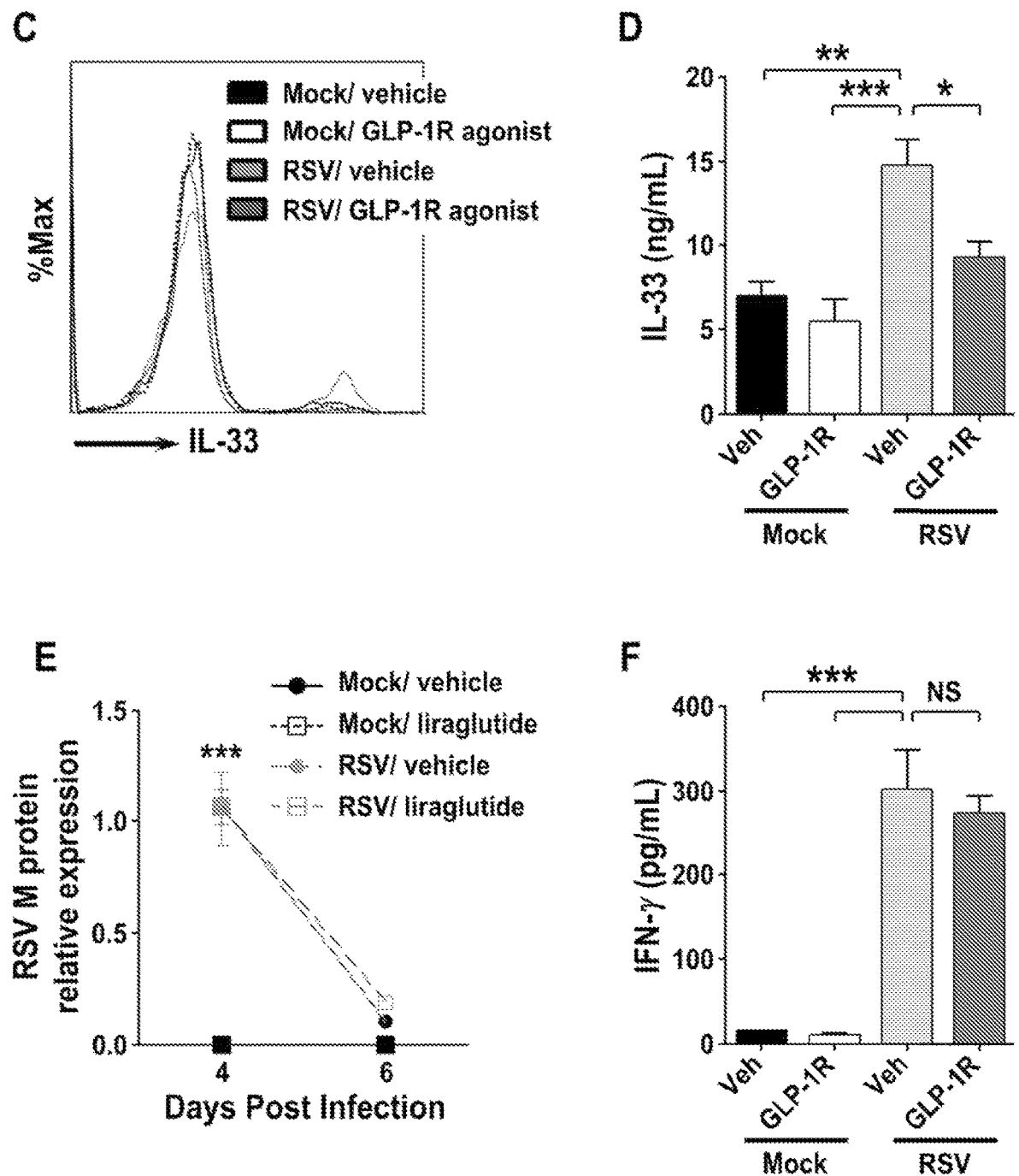
Figure 8:
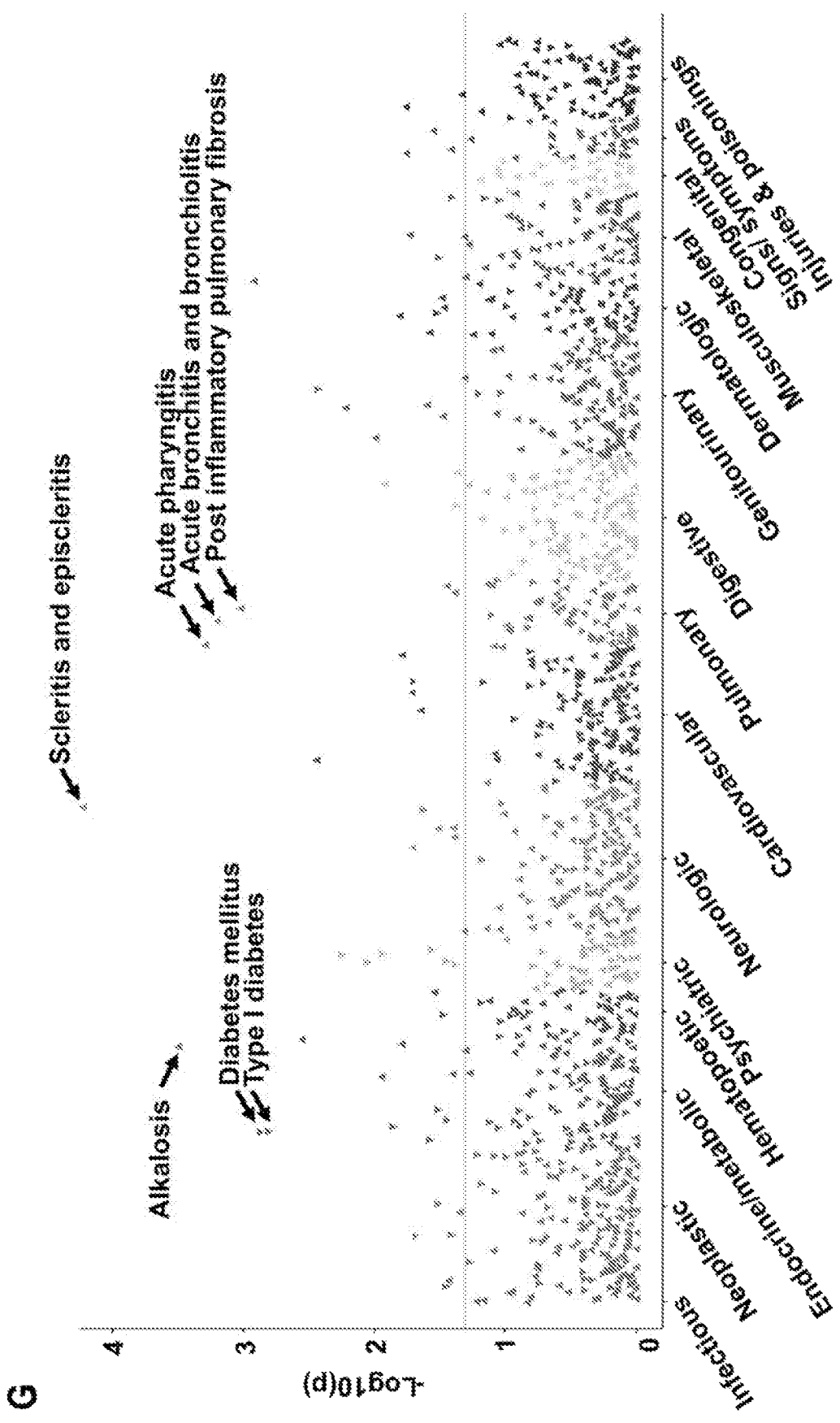

IL-33 activates type 2 cytokine-producing immune cells including ILC2, Th2, and basophils. Il33$^{Citrine/+}$ reporter mice were used to examine the effect of GLP-1R signaling on IL-33 expression on a per epithelial cell basis. GLP-1R agonist treatment in RSV-infected mice significantly decreased the total number of cells in the lung, the total number of IL-33-expressing epithelial cells, and the percentage of epithelial cells that were IL-33$^+$ compared to RSV-infected vehicle-treated mice (FIG. 14A-B & FIG. 8, A). There was significantly decreased MFI of IL-33 in the epithelial cells of RSV-infected GLP-1R agonist-treated mice compared to RSV-infected vehicle-treated mice, indicating decreased IL-33 expression on a per epithelial cell basis with GLP-1R agonist treatment (FIG. 8, B-C). RSV-infected GLP-1R agonist-treated mice had significantly decreased lung IL-33 protein expression compared to RSV-infected vehicle-treated mice (FIG. 8, D). These data indicate that GLP-1R agonist treatment inhibits the expression of IL-33 by epithelial cells during RSV infection.

To determine whether GLP-1R agonist treatment had a deleterious effect on viral-associated disease severity parameters, viral load, an indicator of RSV disease severity, was evalauted.[6] There were no significant differences in the viral load between RSV-infected GLP-1R agonist and vehicle-treated mice (FIG. 8, E). Consistent with these data, no significant differences were observed in lung interferon-γ (IFN-γ) expression or IFN-γ$^+$ Th1 and natural killer (NK) cells between RSV-infected GLP-1R agonist and vehicle-treated mice 6 days post-infection (FIGS. 12B&D, FIG. 8, F & FIGS. 15A-B). Further, there were no significant differences in lung IFN-α, IFN-β, or IL-27 protein expression between RSV-infected GLP-1R agonist and vehicle-treated mice (FIG. 15C-E). It was also found that there were no statistically significant changes in plasma glucose or insulin levels with GLP-1R treatment compared to vehicle (FIGS. 15F & G)

To determine whether GLP-1R agonist treatment during primary infection has an impact on the immune response to a later secondary infection, mice were infected with RSV a second time following primary RSV infection (FIG. 16). GLP-1R agonist treatment during primary infection significantly decreased the number of RSV-induced total BAL cells and lymphocytes compared to vehicle treatment after secondary infection (FIG. 17A). The mice treated with GLP-1R agonist during primary infection did not exhibit altered lung IFN-γ expression nor RSV F-protein-specific antibody responses compared to vehicle-treated mice during secondary RSV infection (FIG. 17B-E). These data demonstrate that GLP-1R agonist treatment does not exacerbate disease or impede anti-viral responses.

Next, associations between GLP-1 signaling and human RSV disease were examined. The phenome-wide association study (PheWAS) is a new, validated reverse genetics approach that associates genetic variants of interest with phenotypes by linking a database of de-identified genotyping to a broad range of electronic medical record (EMR)-derived clinical phenotypes. The EMR phenotypes are derived from cluster of common *International Classification of Diseases, Ninth Revision*, codes. The loss-of-function rs7578597 variant of THADA, encoding thyroid adenoma-associated protein, is associated with lower beta-cell response to GLP-1.[7] A PheWAS on the single nucleotide polymorphism (SNP) rs7578597 (missense, T1187A) and 1,000 phenoyptes from the Vanderbilt BioVU biobank of 29,713 individuals of European ancestry (EA)[8] revealed a highly significant association of rs7578597 with acute bronchitis and bronchiolitis (OR=1.24, P=6.3×10$^{-3}$; FIG. 8, G and Table 1).

TABLE 1

PheWAS results for THADA rs7578597 in humans (All phenotypes with p < 0.01 are reported below)

| Phenotype | Cases | Controls | Odds ratio | p |
|---|---|---|---|---|
| Scleritis and episcleritis | 67 | 25573 | 2.33 | 0.00006 |
| Alkalosis | 187 | 18873 | 1.67 | 0.00032 |
| Acute pharyngitis | 798 | 22135 | 1.31 | 0.00051 |
| Acute bronchitis and bronchiolitis | 1223 | 22347 | 1.24 | 0.00063 |
| Postinflammatory pulmonary fibrosis | 349 | 19926 | 1.43 | 0.00094 |
| Diabetes mellitus | 5032 | 21287 | 0.88 | 0.00136 |
| Type 1 diabetes | 468 | 21287 | 0.67 | 0.00157 |
| Morbid obesity | 972 | 24650 | 1.23 | 0.00276 |
| Other forms of chronic heart disease | 1095 | 21791 | 1.22 | 0.00359 |
| Other disorders of male genital organs | 243 | 9538 | 0.58 | 0.00374 |
| Personality disorders | 107 | 20065 | 0.41 | 0.00566 |
| Other symptoms/disorders or the urinary system | 4228 | 21638 | 1.11 | 0.00600 |
| Anxiety, phobic and dissociative disorders | 3229 | 20065 | 0.89 | 0.00884 |

This study is the first investigation of GLP-1R signaling during viral infection. In this example, it was shown that administration of a GLP-1R agonist attenuates type 2-associated immunopathology during RSV infection. This is also the first report of an FDA-approved pharmacologic agent inhibiting lung IL-33 protein expression, and this finding has significant implications as it provides an alternative to biologic therapies such as monoclonal antibodies or receptor antagonists that target IL-33-mediated diseases.[9] Together, these data provide a novel therapeutic for RSV infection, a disease for which there currently is no treatment after infection has occurred.

Abbreviations Used in this Example

ILC2 (group 2 innate lymphoid cells); RSV (respiratory syncytial virus); Th2 (T helper 2); glucagon-like peptide-1 (GLP-1); WT (wild type); MFI (mean fluorescence intensity); PFU (plaque forming unit); PheWAS (phenome-wide association study)

REFERENCES CITED IN THIS EXAMPLE

1. Campbell J E, Drucker D J. Pharmacology, physiology, and mechanisms of incretin hormone action. *Cell Metab.* 2013; 17(6):819-837. doi:10.1016/j.cmet.2013.04.008.
2. Marso S P, Daniels G H, Brown-Frandsen K, Kristensen P, Mann J F E, Nauck M A, Nissen SE, Pocock S, Poulter N R, Ravn L S, Steinberg W M, Stockner M, Zinman B, Bergenstal R M, Buse J B, LEADER Steering Committee, LEADER Trial Investigators. Liraglutide and Cardiovascular Outcomes in Type 2 Diabetes. *N Engl J Med.* 2016; 375(4):311-322. doi: 10.1056/NEJMoa1603827.

3. Ahern T, Tobin A-M, Corrigan M, Hogan A, Sweeney C, Kirby B, O'Shea D. Glucagon-like peptide-1 analogue therapy for psoriasis patients with obesity and type 2 diabetes: a prospective cohort study. *J Eur Acad Dermatol Venereol*. 2013; 27(11):1440-1443. doi:10.1111/j.1468-3083.2012.04609.x.
4. Zhu T, Wu X-L, Zhang W, Xiao M. Glucagon Like Peptide-1 (GLP-1) Modulates OVA-Induced Airway Inflammation and Mucus Secretion Involving a Protein Kinase A (PKA)-Dependent Nuclear Factor-κB (NF-κB) Signaling Pathway in Mice. *Int J Mol Sci*. 2015; 16(9): 20195-20211. doi:10.3390/ijms160920195.
5. Johnson J E, Gonzales R A, Olson S J, Wright P F, Graham B S. The histopathology of fatal untreated human respiratory syncytial virus infection. *Mod Pathol*. 2007; 20(1): 108-119. doi:10.1038/modpathol.3800725.
6. DeVincenzo J P, El Saleeby C M, Bush A J. Respiratory syncytial virus load predicts disease severity in previously healthy infants. *J Infect Dis*. 2005; 191(11):1861-1868. doi:10.1086/430008.
7. Simonis-Bik A M, Nijpels G, van Haeften T W, Houwing-Duistermaat J J, Boomsma D I, Reiling E, van Hove E C, Diamant M, Kramer M H H, Heine R J, Maassen J A, Slagboom P E, Willemsen G, Dekker J M, Eekhoff E M, de Geus E J, 't Hart L M. Gene Variants in the Novel Type 2 Diabetes Loci CDC123/CAMK1D, THADA, ADAMTS9, BCL11A, and MTNR1B Affect Different Aspects of Pancreatic-Cell Function. *Diabetes*. 2010; 59(1):293-301. doi:10.2337/db09-1048.
8. Denny J C, Bastarache L, Ritchie M D, Carroll R J, Zink R, Mosley J D, Field J R, Pulley J M, Ramirez A H, Bowton E, Basford M A, Carrell D S, Peissig P L, Kho A N, Pacheco J A, Rasmussen L V, Crosslin D R, Crane P K, Pathak J, Bielinski S J, Pendergrass S A, Xu H, Hindorff L A, Li R, Manolio T A, Chute C G, Chisholm R L, Larson E B, Jarvik G P, Brilliant M H, McCarty C A, Kullo I J, Haines J L, Crawford D C, Masys D R, Roden D M. Systematic comparison of phenome-wide association study of electronic medical record data and genome-wide association study data. *Nat Biotechnol*. 2013; 31(12):1102-1111. doi:10.1038/nbt.2749.
9. Borish L. The immunology of asthma: Asthma phenotypes and their implications for personalized treatment. *Ann Allergy Asthma Immunol*. 2016; 117(2):108-114. doi:10.1016/j.anai.2016.04.022.

Methods

Virus and Mice.

RSV strain 12/12-6 was isolated in 2012 from a hospitalized infant with severe lower respiratory tract infection and bronchiolitis as part of the INSPIRE study.[1] RSV was propagated and titrated in HEp-2 cells as previously described.[2] Mock inoculum was prepared by collecting cell culture supernatant from lysed, uninfected HEp-2 cells. 8-week old female BALB/cJ mice were purchased from Jackson Laboratories (Bar Harbor, Me.). Il33Citrine/+ reporter mice were generated by crossbreeding WT BALB/c mice and Il33Citrine/Citrine mice that were the kind gift of Dr. Andrew N.J. McKenzie.[3] Mice were maintained under specific pathogen free conditions and used in compliance with the revised 2011 Guide for the Care and Use of Laboratory Animals prepared by the Committee on Care and Use of Laboratory Animals of the Institute of Laboratory Animal Resources, National Research Council.[4] For infection, mice were anesthetized by intraperitoneal injection of ketamine/xylazine solution and inoculated via intranasal delivery with $9 \times 10^5$ PFU of RSV 12/12-6 or an equal volume of mock inoculum as previously described.[5] Weight loss was measured daily. The GLP-1R agonist liraglutide (Novo Nordisk, Plainsboro, N.J.) was initiated at the same dose that is used in patients with Type II Diabetes. This was increased in two-fold increments daily until the final dose of 0.2 mg/kg weight was reached. The vehicle for liraglutide, 0.1% BSA in PBS, was used as a control. Treatment was given subcutaneously beginning 2 days prior to infection or beginning on the same day as infection and given twice daily until the mice were euthanized.

BAL and PAS Staining.

0.8 mL saline was instilled through a tracheostomy tube and withdrawn via syringe to obtain BAL fluid. Total cells were counted on a hemocytometer by using trypan blue exclusion. For cell differentials, 0.1 mL of BAL fluid was prepared via cytospin (Thermo Fisher Scientific, Waltham, Mass.) and subsequently fixed and stained using DiffQuik (American Scientific Products, Columbus, Ohio). Differential counts were based on counts of 200 eosinophils, lymphocytes, or macrophages. For PAS staining, lungs were perfused with PBS, inflated with 10% neutral buffered formalin, and fixed in 10% neutral buffered formalin for 24 hours at room temperature. Lungs were then paraffin embedded, sectioned (5 µm), and stained with periodic acid-Schiff (PAS) to visualize mucus. Small and medium sized airways were scored for mucus by a trained pathologist blinded to the experimental information using the following scoring scheme: (0) no PAS positive cells observed in cross sections of medium to small airways; (1) less than 10 PAS positive cells observed in cross sections of medium to small airways; (2) greater than 10 PAS positive cells observed in cross sections of medium to small airways; or (3) greater than 10 PAS positive cells observed in cross sections of medium to small airways with mucous strands observed in air spaces.

Airway Responsiveness.

Airway responsiveness was measured as previously described.[6,7] Briefly, mice were anesthetized with an intraperitoneal injection of pentobarbital sodium (85 mg/kg). A tracheostomy tube was inserted for ventilation. The internal jugular vein was cannulated for intravenous delivery of acetyl-β-methacholine. The mice were then placed in a whole-body plethysmography chamber and mechanically ventilated. Precision glass microsyringes were used to deliver increasing doses of acetyl-β-methacholine. Baseline airway resistance measurements were collected followed by measurements with 137, 411, 1233, and 3700 µg/kg body weight of acetyl-β-methacholine (Sigma-Aldrich, Saint Louis, Mo.). Peak airway resistance measurements for each dose were recorded.

ELISA.

Lungs were snap-frozen in liquid nitrogen at the time of harvest. Lungs were mechanically disrupted using 1 mL of MEM media and homogenized via BeadBeater (BioSpec Products, Bartlesville, Okla.). Protein measurements were performed using either Duoset (IL-33), Quantikine (IL-13, IFN-γ, and IL-27), or Verikine (IFN-α and IFN-β) enzymelinked immunosorbent assay (ELISA) kits according to manufacturer instructions 53 (R&D Systems, Minneapolis, Minn.). Serum RSV F-protein-specific antibody was measured as previously described.[2]

Flow Cytometry.

Lungs were harvested, minced, and digested in RPMI media with 5% FBS, 1 mg/mL collagenase, and 0.02 mg/mL DNase I for 40 minutes at 37° C. The digestion was stopped with 100 µl of 0.5 M EDTA, and a single cell suspension was generated by straining these digestions through a 70 µm filter. RBC lysis (BioLegend, San Diego, Calif.) was performed according to manufacturer instructions. Cells were stimulated in IMDM media with 10% FBS, 0.01 mM non-essential amino acids, penicillin/streptomycin, 1 mM sodium pyruvate, 10 ng/mL PMA, 1 µM ionomycin, and 0.07% monensin for 4 hours at 37° C. Cells were stained with Live/Dead Blue (Life Technologies, Carlsbad, Calif.) and combinations of the following surface markers: CD45 (30-F11), CD25 (PC61.5), FcεR1 (MAR-1), DX5 (DX5), FcεR1 (MAR-1), and NKG2D (CX5) from eBioscience (San Diego, Calif.); CD127 (SB/199), CD3 (17A2), CD146 (ME-9F1), and EpCAM (G8.8) from BioLegend (San Diego, Calif.); CD4 (H129.19) from BD Biosciences (San Jose, Calif.); and/or a surface marker cocktail containing CD5, CD45R (B220), CD11b, Gr-1 (Ly-6G/C), 7-4, and Ter-119 from Miltenyi (Bergisch Gladbach, Germany). Cells were fixed/permeabilized for 12 hours in Cytofix/Cytoperm (BD Biosciences) and stained with combinations of the following intracellular markers: IL-13 (eBio13A) and IFN-γ (XMG1.2) from eBioscience. Anti-FcR antibody (BD Biosciences) was used to prevent nonspecific staining. All samples were run on a BD LSR II Flow Cytometer and analyzed using FlowJo (Version 10; Treestar, Ashland, Oreg.). ILC were defined as Lineage-CD45+ CD25+ CD127+ cells where Lineage (Lin) includes (CD3, CD5, CD45R [B220], CD11b, Gr-1 [Ly-6G/C], 7-4, and Ter-119). ILC2 were defined as ILC that expressed IL-13. Th cells were defined as CD3+ CD4+ cells, basophils were defined as DX5+ FcεR1+ cells, NK cells were defined as CD3− DX5+ cells, and epithelial cells were defined as CD45− CD146+ EpCAM+ cells. MFI was determined as the geometric mean.

Viral Load.

Lungs were snap-frozen in liquid nitrogen at the time of harvest. Thawed lungs were resuspended in 1 mL of sterile MEM media or TRIzol reagent (Invitrogen, Carlsbad, Calif.) and homogenized via BeadBeater (BioSpec Products). Total RNA was isolated using TRIzol reagent and cDNA was generated for qPCR analysis of RSV-M and GAPDH. Commercially available primers and probes for GAPDH were used (Applied Biosystems, Foster City, Calif., catalog number 4331182). Custom primers were designed to measure RSV-M.[8] Gene expression was normalized to GAPDH before the fold change was calculated. The fold change in gene expression was calculated via the comparison of gene expression to that of lungs from RSV infected, vehicle-treated mice. Primer sequences were as follows: RSV-M: forward, 5'-GGCAAATATGGAAACATACGTGAA-3' (SEQ ID NO:1), reverse, 5'-TCTTTTTCTAGGACAT-TGTAYTGAACAG-3' (SEQ ID NO:2) (wherein Y is C or T).

Antibody ELISA.

Ectodomain F protein from RSV A2 was fused to a GCN4 trimerization domain and a His tag and expressed in mammalian cells, as previously described.[9] Immulon 2B (Thermo Scientific, Rochester, N.Y.) plates were coated with 150 ng of RSV F protein in PBS overnight at 4° C. Plates were blocked with 1% BSA in PBS for 1 hour at room temperature. Supernatants were serially diluted 1:2 starting at 1:80 over 6 total dilutions, and plates were incubated for 1 hour at room temperature. RSV-specific antibody was detected using horseradish peroxidase-conjugated goat anti-mouse antibody specific for mouse IgG (1:5,000), IgG1 (1:500), or IgG2a (1:500) for 1 hour at room temperature (Southern Biotech, Birmingham, Ala.). Plates were developed in Ultra-TMB (Pierce, Rockford, Ill.) and the reaction was stopped with 1M HCl. Absorbance values (450 nm) were measured and assessed using Gen 5 software (BioTk, Vinooski, Vt.). The serum endpoint dilution at 0.2 absorbance units above background (PBS blank) was calculated for each antibody type.

Statistical Analysis.

Groups were compared using unpaired t-test, one-way analysis of variance (ANOVA) with Bonferroni post-test, or two-way ANOVA with Dunn's multiple comparison test, as appropriate with GraphPad Prism (Version 5; GraphPad Software, San Diego, Calif.). Measurements below the limit of detection were assigned half of the value of the limit of detection for statistical comparisons.

PheWAS Study.

To investigate possible human associations with THADA variation, a population of 29,713 individuals of European ancestry were used who had genotyping on Illumina HumanExome BeadChip version 1.1 and available electronic medical record (EMR) data from the Vanderbilt BioVU DNA biobank.[10] This platform contained the THADA single nucleotide polymorphism (SNP) rs7578597, which corresponds to a threonine to alanine in multiple splice variants. The minor T allele of rs7578597 was present in 11% of individuals. All phenotypes defined were evaluated using a PheWAS of this SNP using previously described methods.[11] Briefly, the method defines cases for 1,000 phenotypes by the presence of specific *International Classification of Diseases, Ninth Revision* (ICD9), codes on at least two different days. Controls for each phenotype are defined as individuals who lack case ICD9 codes and other codes that are related. For example, cases of the "acute bronchitis and bronchiolitis" phenotype are defined with the ICD9 code 483, while its controls are defined as absence of the 483 ICD9 codes. Version 1.2 of the PheWAS code terminology system was used and the R PheWAS package to calculate the PheWAS and graph results,[12] both of which can be downloaded from http://phewascatalog.org. Logistic regression was used for each phenotype with 40 cases or more, adjusted for age and sex, assuming an additive genetic model.

REFERENCES CITED IN THE METHODS SECTION IN THIS EXAMPLE

1. Larkin, E. K. et al. Objectives, design and enrollment results from the Infant Susceptibility to Pulmonary Infections and Asthma Following RSV Exposure Study (INSPIRE). *BMC Pulm. Med.* 15, 45 (2015).
2. Dulek, D. E. et al. STAT4 Deficiency Fails To Induce Lung Th2 or Th17 Immunity following Primary or Secondary Respiratory Syncytial Virus (RSV) Challenge but Enhances the Lung RSV-Specific CD8+ T Cell Immune Response to Secondary Challenge. *J. Virol.* 88, 9655-72 (2014).
3. Hardman, C. S., Panova, V. & McKenzie, A. N. J. IL-33 citrine reporter mice reveal the temporal and spatial expression of IL-33 during allergic lung inflammation. *Eur. J. Immunol.* 43, 488-98 (2013).
4. Animals, N. R. C. (US) C. for the U. of the G. for the C. and U. of L. *Guide for the Care and Use of Laboratory Animals.* (National Academies Press, 2011). doi: 10.17226/12910
5. Graham, B. S., Perkins, M. D., Wright, P. F. & Karzon, D. T. Primary respiratory syncytial virus infection in mice. *J. Med. Virol.* 26, 153-62 (1988).
6. Peebles, R. S., Sheller, J. R., Johnson, J. E., Mitchell, D. B. & Graham, B. S. Respiratory syncytial virus infection prolongs methacholine-induced airway hyperresponsiveness in ovalbumin-sensitized mice. *J. Med. Virol.* 57, 186-92 (1999).
7. Peebles, R. S. et al. Respiratory syncytial virus infection does not increase allergen147 induced type 2 cytokine production, yet increases airway hyperresponsiveness in mice. *J. Med. Virol.* 63, 178-88 (2001).
8. Kodani, M. et al. Application of TaqMan low-density arrays for simultaneous detection of multiple respiratory pathogens. *J. Clin. Microbiol.* 49, 2175-82 (2011).
9. Bates, J. T. et al. Reversion of somatic mutations of the respiratory syncytial virus specific human monoclonal antibody Fab19 reveal a direct relationship between association rate and neutralizing potency. *J. Immunol.* 190, 3732-9 (2013).
10. Roden, D. et al. Development of a Large-Scale De-Identified DNA Biobank to Enable Personalized Medicine. *Clin. Pharmacol. Ther.* 84, 362-369 (2008).
11. Denny, J. C. et al. Systematic comparison of phenome-wide association study of electronic medical record data and genome-wide association study data. *Nat. Biotechnol.* 31, 1102-1111 (2013).
12. Carroll, R. J., Bastarache, L. & Denny, J. C. R PheWAS: data analysis and plotting tools for phenome-wide association studies in the R environment. *Bioinformatics* 30, 2375-2376 (2014).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method of ameliorating the symptoms of an allergic disease in a human subject who has an allergic disease induced by protease-containing aeroallergens, comprising administering to the human subject a therapeutically effective amount of liraglutide to the human subject.

2. The method of claim 1, wherein the allergic disease is selected from the group consisting of allergic lung disease, asthma, allergen-induced airway hyperresponsiveness, allergen-induced inflammation, rhinitis, allergic rhinitis, eosinophilic esophagitis, atopic dermatitis, occupational allergy, allergic conjunctivitis, hay fever, airborne allergic sensitivities, hypersensitivity pneumonitis, and eosinophilic lung diseases.

3. The method of claim 2. wherein the allergic disease is allergic lung disease.

4. The method of claim 2, wherein the allergic disease is asthma.

5. The method of claim 1, comprising administering to the subject a therapeutically effective amount of liraglutide to the subject in an amount from 0.6 mg to 1.8 mg per day.

* * * * *

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Synthetic construct

<400> SEQUENCE: 1
ggcaaatatg gaaacatacg tgaa                                              24

<210> SEQ ID NO 2
<211> LENGTH: 28
<212> TYPE: DNA
<213> ORGANISM: Artificial Sequence
<220> FEATURE:
<223> OTHER INFORMATION: synthetic construct; Y can be C or T

<400> SEQUENCE: 2 tcttttcta ggacattgta ytgaacag                                           28
```